US 8,747,382 B2

(12) United States Patent
D'Souza et al.

(10) Patent No.: US 8,747,382 B2
(45) Date of Patent: Jun. 10, 2014

(54) TECHNIQUES FOR COMPENSATING MOVEMENT OF A TREATMENT TARGET IN A PATIENT

(75) Inventors: Warren D'Souza, Timonium, MD (US); Hao Zhang, Baltimore, MD (US); Kathleen Malinowski, Annapolis, MD (US)

(73) Assignees: University of Maryland, Baltimore, Baltimore, MD (US); University of Maryland, College Park, College Park, MD (US)

( * ) Notice: Subject to any disclaimer, the term of this patent is extended or adjusted under 35 U.S.C. 154(b) by 366 days.

(21) Appl. No.: 13/172,010

(22) Filed: Jun. 29, 2011

(65) Prior Publication Data

US 2012/0004518 A1    Jan. 5, 2012

Related U.S. Application Data

(63) Continuation-in-part of application No. 11/911,514, filed on Dec. 27, 2007, now Pat. No. 8,042,209.

(60) Provisional application No. 60/671,389, filed on Apr. 13, 2005.

(51) Int. Cl.
*A61M 31/00* (2006.01)

(52) U.S. Cl.
USPC .......................................................... 604/500

(58) Field of Classification Search
USPC .......... 604/500–522, 19–21; 378/65, 64, 205, 378/208–209; 128/897; 5/610, 607, 601, 5/600
See application file for complete search history.

(56) References Cited

U.S. PATENT DOCUMENTS

| 4,043,324 A | 8/1977 | Shaw, IV |
| 4,150,292 A | 4/1979 | Ter-Pogossian |
| 4,629,989 A | 12/1986 | Riehl et al. |
| 5,090,401 A | 2/1992 | Schwieker |
| 5,099,855 A | 3/1992 | Yount |
| 6,118,848 A | 9/2000 | Reiffel |
| 6,144,875 A | 11/2000 | Schweikard et al. |

(Continued)

FOREIGN PATENT DOCUMENTS

| DE | 19614643 A1 | 10/1997 |
| DE | 19728788 A1 | 1/1999 |

(Continued)

OTHER PUBLICATIONS

Achim Schweikard et al., "Robotic Motion Compensation for Respiratory Movement During Radiosurgery", Computer Aided Surgery, 2000, 16 pages.

(Continued)

*Primary Examiner* — Manuel Mendez
(74) *Attorney, Agent, or Firm* — Squire Sanders (US) LLP

(57) ABSTRACT

One embodiment includes a method of predicting a position of a target site inside a body using surrogates is provided. The method includes transforming surrogate measurements and target positions into different representations by applying an operator, establishing a special relationship between the transformed surrogate measurements and the transformed target positions, and continuously predicting the target position from the transformed surrogate measurements and the established special relationship.

24 Claims, 8 Drawing Sheets

(56) References Cited

U.S. PATENT DOCUMENTS

| | | |
|---|---|---|
| 6,292,682 B1 | 9/2001 | Kruger |
| 6,374,667 B1 | 4/2002 | Eriksen et al. |
| 7,154,991 B2 | 12/2006 | Earnst et al. |
| 8,042,209 B2 * | 10/2011 | D'Souza et al. .................. 5/610 |
| 2002/0193685 A1 | 12/2002 | Mate et al. |
| 2007/0015991 A1 | 1/2007 | Fu et al. |

FOREIGN PATENT DOCUMENTS

| | | |
|---|---|---|
| DE | 10161152 A1 | 6/2003 |
| WO | 2005/039472 A2 | 5/2005 |
| WO | 2006/113323 A2 | 10/2006 |

OTHER PUBLICATIONS

Marcus Isaksson et al., "On Using an Adaptive Neural Network to Predict Lung Tumor Motion During Respiration for Radiotherapy Applications", Med. Phys. 32, Dec. 2005, 10 pages.

European Search Report application No. 12174049.2 dated Sep. 19, 2012.

Final Office Action, dated Mar. 21, 2011, in U.S. Appl. No. 11/911,514.

European Search Report application No. 06758323.7 dated Aug. 8, 2011.

Office Action dated Jan. 28, 2014, issued in corresponding Canadian patent application No. 2,781,536.

\* cited by examiner

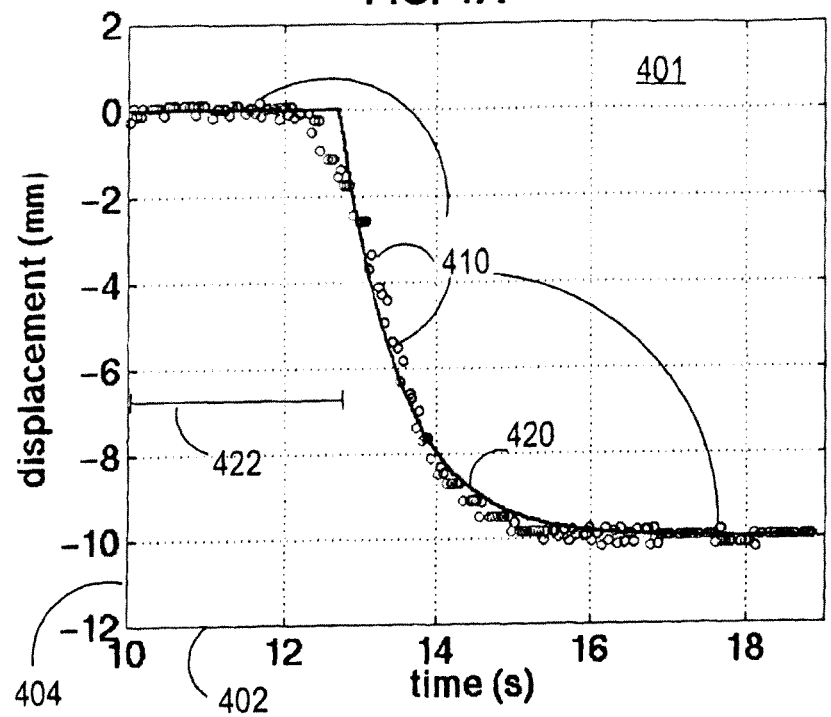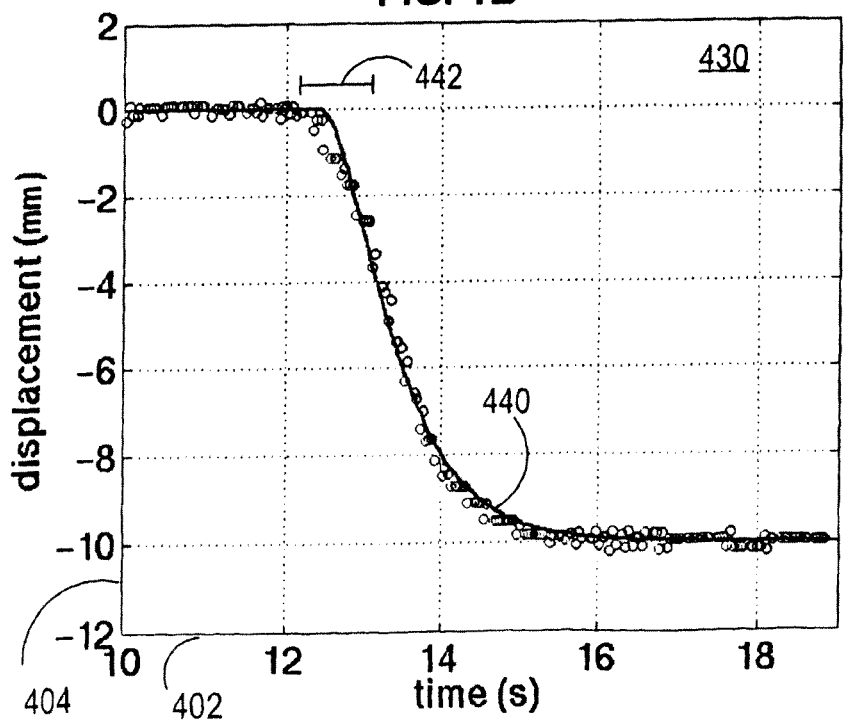

TECHNIQUES FOR COMPENSATING MOVEMENT OF A TREATMENT TARGET IN A PATIENT

CROSS-REFERENCE TO RELATED APPLICATIONS

This application is a continuation in part of application Ser. No. 11/911,514 filed on Dec. 27, 2007, which claims priority from Provisional Appln. No. 60/671,389, filed Apr. 13, 2005. The entire contents of these earlier filed applications are hereby incorporated by reference in their entirety as if fully set forth herein.

STATEMENT OF GOVERNMENTAL INTEREST

This invention was made with Government support under Grant No. CA124766 awarded by the National Institutes of Health. The Government has certain rights in the invention.

BACKGROUND OF THE INVENTION

1. Field of the Invention

The present invention relates to treatment of tissues in a living organism, and in particular to moving a support structure or treatment delivery device, or both, to compensate for tissue movement relative to the treatment delivery device caused by biological activity of the organism, such as respiration, during treatment delivery, such a during delivery of a dose of radiation. Embodiments of the invention are also directed to a method and/or device for predicting the position of a target site, such as a tumor, inside a human or other animal body in real time or near real time using surrogates.

2. Description of the Related Art

Tumors in the thoracic and abdominal regions are susceptible to motion during normal respiration. Treating these tumors with, for example, a radiation beam or zone must take into account this moving target. Uncorrected, this leads to at least part of the tumor receiving less than the desired dose while that part is outside the treatment zone. Conventional methods to account for this problem involve the addition of a "treatment margin" so that a greater volume of tissue, including normal healthy tissue, is treated to therapeutic doses. Subjecting normal tissue to therapeutic doses can lead to possible complications.

Studies in the thorax and abdomen have shown that respiration can cause tumors to move up to 2 cm (see, for example, Kitamura K, Shirato H, Seppenwoolde Y, Shimizu T, Kodama Y, Endo H, Onimaru R, Oda M, Fujita K, Shimizu S, Miyasaka K. Tumor location, cirrhosis, and surgical history contribute to tumor movement in the liver, as measured during stereotactic irradiation using a real-time tumor-tracking radiotherapy system. *Int J Radiat Oncol Biol Phys*. vol. 56, pp 221-228, 2003). Although 3-D conformal and intensity-modulated radiation therapy (IMRT) can potentially deliver highly conformal doses to the tumor while sparing normal healthy tissues, respiration-induced tumor motion can produce under-dosing of the tumor's periphery (see, for example, Bortfeld T, Jokivarski K, Goitein M, Kung J, Jiang S B. Effects of intra-fraction motion on IMRT dose delivery: statistical analysis and simulation. *Phys Med Biol* vol. 47, pp 2203-2220, 2002; and Naqvi S A, D'Souza W D. A stochastic convolution/superposition method with isocenter sampling to evaluate intrafraction motion effects in IMRT. *Med Phys* vol. 32, pp 1156-1163, 2004).

Conventional methods to deal with tumor motion have involved allowing an adequate margin when designing the treatment fields or defining the planning tumor volume (PTV). Advanced methods to manage respiratory-induced tumor motion during radiation delivery include breath-holds, both voluntary (see, for example, Rosenzweig K E, Hanley J, Mah D, Mageras G, Hung M, Toner S, Burman C, Ling C C, Mychalczak B, Fuks Z, and Leibel S A. The deep inspiration breath-hold technique in the treatment of inoperable non-small-cell lung cancer. *Int J Radiat Oncol Biol Phys* vol. 48, pp 81-87, 2000) and forced (see, for example, Dawson L A, Brock K K, Kazanjian S, Fitch D, McGinn C J, Lawrence T S, Ten Haken R K, Balter J. The reproducibility of organ position using active breathing control (ABC) during liver radiotherapy. *Int J Radiat Oncol Biol Phys* vol. 51, pp 1410-1421, 2001), beam gating (see, for example, Shirato H, Shimizu S, Kunieda T, Kitamura K, van Herk M, Kagei K, Nishioka T, Hashimota S, Fujita K, Aoyama H, Tsuchiya K, Kudo K, and Miyasaka K. Physical aspects of a real-time tumor-tracking system for gated radiotherapy. *Int J Radiat Oncol Biol Phys* vol. 48, pp 1187-1195, 2000) and real-time tumor tracking. Tumor-tracking using conventional linear accelerators for beam delivery is conventionally based on moving a multi-leaf collimator (MLC). (See for example, Keall P J, Kini V R, Vedam S S, and Mohan R. Motion adaptive x-ray therapy: a feasibility study. *Phys Med Biol* vol. 46, pp 1-10, 2001, the entire contents of which are herby incorporated by reference as if fully set forth herein). Tracking using repositioning of the linear accelerator has also been described (Adler J R, Murphy M J, Chang S D. Image-guided robotic radiosurgery. *Neurosurgery* vol. 44, pp 1299-1307, 1999; Schweikard A, Glosser G, Bodduluna M, Murphy M J, and Adler J R. Robotic motion compensation for respiratory movement during radiosurgery. *Comput Aided Surg* vol. 5, pp 263-277, 2000; Ozhasoglu C and Murphy M J. Issues in respiratory motion compensation during external-beam radiotherapy. *Int J Radiat Oncol Biol Phys* vol. 52, pp 1389-1399, 2002, the entire contents of each of which are herby incorporated by reference as if fully set forth herein). A CYBERKNIFE™ from Accuray Inc. of Sunnyvale, Calif., uses a miniaturized linear accelerator mounted on an industrial robot.

Methods for managing respiration-induced motion while a fraction of the radiation dose (or other treatment) is delivered (called herein "intra-fraction" motion) may be broadly grouped into breath-hold methods, gating methods and real-time tracking methods. Breath-hold and gating techniques pose the disadvantage of increased treatment time. The duty cycle for gating is typically 25% on and 75% off, because the beam is turned on during a specific "window" of the respiration cycle and turned off the remainder. Because the total treatment time for IMRT is longer than conventional delivery, further increasing the treatment time with breath-holds and gating only increases the probability of spurious intra-fraction patient motion (such as shifting unrelated to respiration). In addition breath-holds are uncomfortable, particularly for patients with compromised pulmonary capacity. With this type of motion management, the radiation can only be delivered during breath-holds which may last 10-20 s or less, depending on the patient's ability to hold their breath. The time of treatment delivery assumes even more significant role in IMRT treatments. Each 3-D conformal field can be delivered in 1-2 breath-hold cycles. However IMRT treatments involve 2-10 times as many monitor units (a measure of radiation dose delivered to a patient), and thus involve up to about 20 breath holds. Thus breath-holds during IMRT treatments not only prolong the treatment time, but also make it difficult for patients, who increasingly fatigue as treatment progresses. Hence, such respiration management strategies may not be applicable to a significant population of patients.

Gating techniques involve radiation delivery during a pre-defined window of the respiration cycle. The duty cycle is typically 25%. Thus 75% of the time the patient receives no treatment as the tumor target is out of range. In addition, tumor motion can still occur during the gating interval. If the amplitude of this motion is significant, it could adversely impact the planned dose distribution. As with breath-holds, gating methods prolong time for treatment delivery thereby increasing the chances of spurious patient motion.

Tumor-tracking methods have distinct advantages over breath-holds and gating methods by reducing treatment delay and patient discomfort. However, they are technically more challenging. In one approach, tumor-tracking adjusts the linear accelerator or its collimator (e.g., the multi-leaf collimator, MLC) to keep the moving tumor in focus. One method is to use multiple sets of CT images each associated with a specific breathing phase measured using some type of breathing sensor or a surrogate measure. Another method is to use simultaneous x-ray imaging of implanted markers under fluoroscopy and breathing monitoring using sensors or other surrogates. During delivery, the radiation starts at a pre-determined phase, at which the radiation beam is pointed at the target corresponding to this breathing phase. Patient breathing is continuously monitored and the position of the tumor is determined according to the predetermined relationship. Ideally, the beam is adjusted in real-time based on the breathing signal to track the movement of the target. However, after determining the current position of the tumor, there is some finite time delay in the displacement response of the MLC.

Furthermore, use of the MLC to follow movement reduces the capacity of the MLC to provide intensity modulation in multiple planes and increases wear on an expensive and sensitive piece of equipment. An MLC can compensate for tumor motion in two dimensions only, and the spatial resolution in one direction is limited by the width of the leaf (e.g. 0.5 cm). For an MLC, beam alignment (or control) relative to the tumor can be maintained only in the plane of treatment field. If the tumor moves out of plane, the treatment plan integrity may be compromised. Additionally, intensity-modulated radiation therapy (IMRT) and intensity modulated arc delivery (IMAT) involve significant physical movement on the part of the MLC to begin with, especially, when one considers that as many as 30% of the patients in our clinic are treated with IMRT for various disease sites. To further impose a breathing-induced motion on the MLC could exceed the physical limits of the device, such as leaf speed. Such additional motion will also lead to excessive wear and tear on the MLC and shorten its lifespan. Excessive motion of the MLC also requires frequent calibration of the MLC since individual leaves have been known to lose their calibration due to overuse For periodic motion, such as respiratory motion, advanced prediction methods such as the use of an adaptive filter (Ozhasoglu, C. and Murphy, M J., Issues in respiratory motion compensation during external-beam radiotherapy. *Int J Radiat Oncol Biol Phys* vol. 52, pp 1389-1399, 2002) have been proposed. It has also been shown that the reproducibility of respiration patterns can be improved with audio visual aids and patient coaching (Vedam S S, Kini V R, Keall P J, Ramakrishnan V, Mostafavi H, Mohan R., Quantifying the predictability of diaphragm motion using an external respiratory signal. *Med Phys* vol. 30, pp 505-513, 2003). However, methods that involve control of patient action may not be suitable for all patients.

Based on the foregoing, there is a clear need for patient treatment delivery techniques that do not suffer all the deficiencies in prior art approaches. In particular, there is a need to track tumor motion in real time that accounts for differences between pre-treatment breathing patterns and breathing patterns during treatment. There is an independent need for techniques to compensate for tumor motion without movement of a treatment delivery device, such as an accelerator or a multi-leaf collimator (MLC).

SUMMARY OF THE INVENTION

Techniques are provided for improving treatment delivered to a target site that moves in a patient during treatment delivery.

In one set of embodiments, a method includes delivering a treatment from a treatment delivery device to a target site in a patient supported by a patient support structure. During the treatment, a state of the patient is measured to produce real-time measurement data. Measuring the state does not invade a body of the patient; and the measured state of the patient is a correlated surrogate for position of the target site. Compensating movement data is determined based on the real-time measurement data to cause the patient support structure to move so that the target site maintains a particular spatial relationship with the treatment delivery device. The patient support structure is moved based on the compensating movement data.

In another set of embodiments, a particular correlation between a position of a target site in a patient and a state of the patient is determined This is done with the following steps. A series of measurements of the state of the patient, which are measured in real time and do not involve invading a body of the patient, are received. A series of temporally separated tomographic images of the target site in the patient are received, which overlap in time the series of measurements of the patient state. A series of temporally separated positions for the target site are determined based on the series of temporally separated tomographic images. Partial least squares (PLS) is applied to the series of patient state measurements and the series of target site positions to determine the particular correlation between the patient state measurements and the target site positions.

In another set of embodiments, a method includes determining an internal controller response function based on inverting at least a portion of a response function for moving a component of a treatment delivery system. The component is a treatment delivery device or a patient support platform. Treatment is delivered from the treatment delivery device to a target site in a patient supported by the patient support structure. During treatment, a state of the patient is measured to produce real-time measurement data. Measuring the state does not invade a body of the patient and the measured state of the patient is a correlated surrogate for position of the target site. Compensating movement data to cause the target site to maintain a particular spatial relationship with the treatment delivery device is determined based on the real-time measurement data and the internal controller response function. The compensating movement data is sent to the moving component to maintain the particular spatial relationship between the target site and the treatment delivery device.

In another set of embodiments, a method of predicting a position of a target site inside a body using surrogates is provided. The method includes transforming surrogate measurements and target positions into different representations by applying an operator, establishing a special relationship between the transformed surrogate measurements and the transformed target positions, and continuously predicting the target position from the transformed surrogate measurements and the established special relationship.

In another set of embodiments, a method includes adjusting a radiotherapy treatment of a target site that moves during the treatment. The adjusting is performed by using a predicted position of the target site in real time or near real time. In one embodiment, the position is predicted by measurement of one or more surrogates irrespective of the quality (e.g., good or poor) and type (e.g., linear, non-linear or other) of relationship (e.g., correlation) between the surrogates and the target site. The position is predicted without periodic or continual use of a direct measurement of the target site.

In other sets of embodiments, an apparatus and a computer-readable medium provide the improved delivery of treatment.

BRIEF DESCRIPTION OF THE DRAWINGS

The present invention is illustrated by way of example, and not by way of limitation, in the figures of the accompanying drawings and in which like reference numerals refer to similar elements and in which:

FIG. 4A is a graph that illustrates the measured response of an existing couch and first order model with dead time fit to the measurements, according to an embodiment;

FIG. 4B is a graph that illustrates the measured response of the existing couch and second order model with dead time fit to the measurements, according to an embodiment;

DETAILED DESCRIPTION

Figure 1:
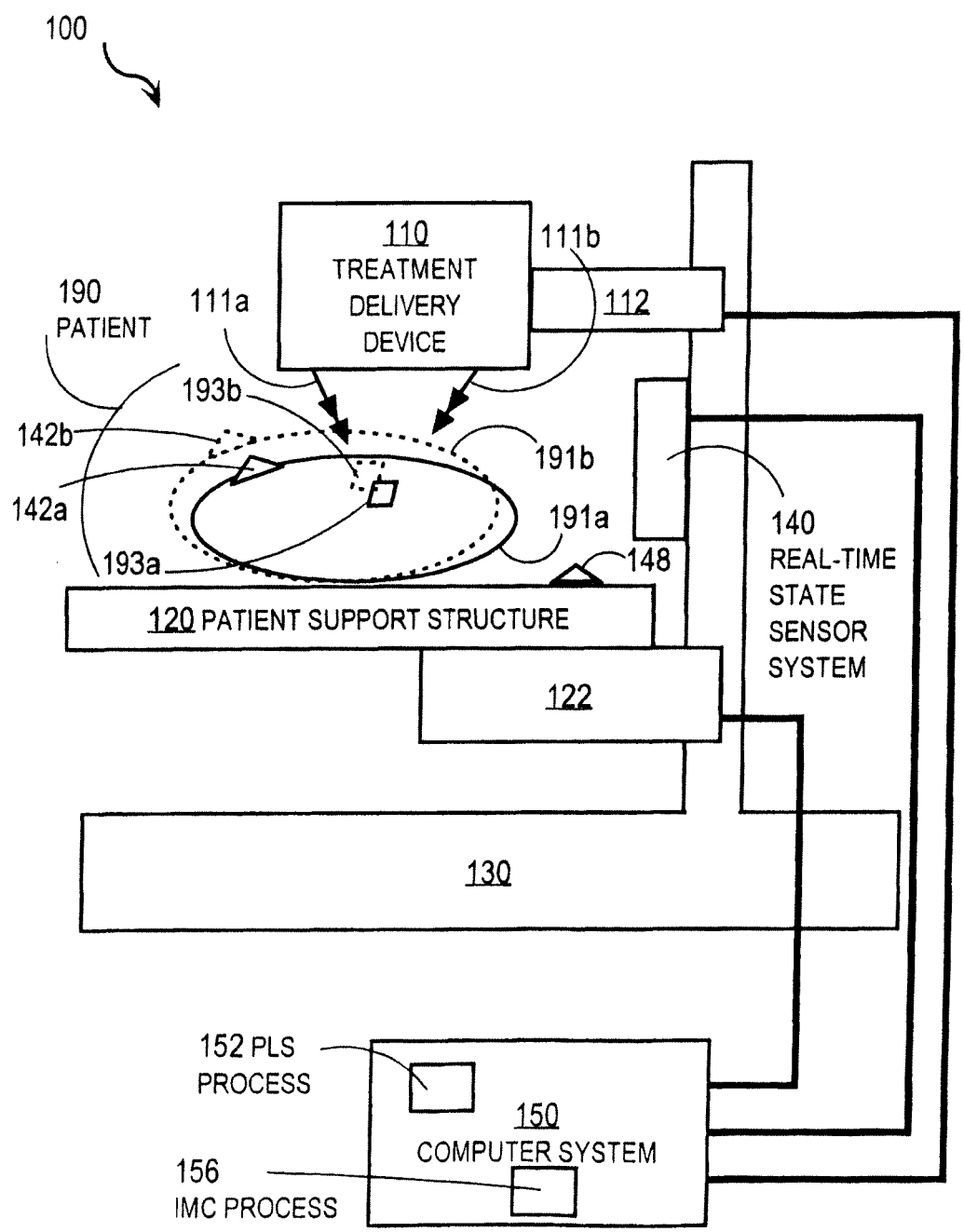
FIG. 1 is a block diagram that illustrates a treatment delivery system in which motion of a target site in a patient is compensated, according to an embodiment.

A method and apparatus are described for improving treatment delivered to a moving target site in a patient. In the following description, for the purposes of explanation, numerous specific details are set forth in order to provide a thorough understanding of the present invention. It will be apparent, however, to one skilled in the art that the present invention may be practiced without these specific details. In other instances, well-known structures and devices are shown in block diagram form in order to avoid unnecessarily obscuring the present invention.

Embodiments of the invention are described in the context of delivering multiple fractional doses of radiation onto a tumor in the thoracic region, such as a tumor in the human breast, lung or liver, while the patient takes several breaths that move the tumor. However, the invention is not limited to this context. In other embodiments, tumor or other tissues or organs in the same or other portions of the patient body that move during treatment or diagnosis, for human or non-human patients, are treated with radiation or other treatments. As used herein, the term target site refers to any tissue or organ in a human or non-human living patient to which treatment is to be delivered. As used herein, the term treatment includes both therapeutic and diagnostic actions by a health care provider. For example, in some embodiments, a hypodermic needle is injected by machine into a tissue in the moving portion of a body to administer an agent or to extract a biopsy.

In some embodiments, a robotic couch moves during treatment in response to organ motion to maintain a target within the treatment zone. Articulated couches with actuators to move under machine control to position a patient prior to treatment are known in the art, but are not shown or suggested or designed to be used for dynamic adjustment during treatment. In the illustrated embodiments, the treatment couch is made to translate, or translate and rotate, as a counter reaction to the motion of the tumor; thereby canceling tumor motion and keeping the tumor at a fixed location (a "set point") relative to the treatment delivery device (e.g., the radiation beam source). However, the invention is not limited to such embodiments. In other embodiments, other portions of the treatment delivery system, such as the treatment delivery device, are moved, alone or in combination with the couch.

For radiation therapy with a conventional linear accelerator, couch-based tracking offers several advantages over multi-leaf collimator (MLC)-based tracking: 1) couch-based tracking affords more degrees of freedom, both translational and rotational, enabling the tracking of out-of-plane movements; and 2) for dynamic intensity-modulated radiation therapy (IMRT) delivery, separating the MLC and couch functions allows the MLC to be used for beam modulation exclusively while the couch can be used in real-time to adapt for tumor motion. This separation decreases the complexity of the delivery and lessens wear-and-tear on the MLC hardware. Moreover, for MLC-based tracking, the MLC motion is the sum of the movements required for target tracking and for intensity-modulation. Having the MLC dedicated for intensity modulation alone reduces the chance of exceeding the physical limits of the MLC.

Some embodiments are effective to spare non-target volumes from radiation, for example, relative to methods that expand the planning tumor volume (PTV). Some embodiments reduce an amount of time a radiation device is active for treating an individual patient, for example, relative to breath-holding and gating methods.

To more particularly describe some embodiments of the invention, couch sizes and ranges of motion, such as specific lag times between detected and compensated motion, are enumerated in the following. These numeric values are not intended to be limiting. In other embodiments for other applications, a practitioner can easily determine through experimentation the size and response characteristics to satisfy a different therapeutic or diagnosis regimen based on the approaches described herein.

1. Structural Overview

FIG. 1 is a block diagram that illustrates a treatment delivery system 100 in which motion of a target site in a patient is compensated, according to an embodiment. Also shown in FIG. 1 is a patient 190, including patient cross-sections 191a and 191b and target site positions 193a and 193b. However, patient 190 is not part of system 100, but merely serves to show how operating properties of system 100 relate to the patient as a subject of system operations. In FIG. 1, the position and shape of the patient is depicted at two times, such as at two different phases of a patient breathing-cycle. At a first time, the patient cross section 191a is shown with a solid perimeter oval. A position 193a of the target site within the patient at the first time is shown with a solid perimeter parallelogram. At the second time, the patient cross section 191b and target site position 193b are shown with dashed perimeter oval and parallelogram, respectively. The challenge is to deliver treatment to the target site as it moves to different positions 193a and 193b at different times during treatment delivery.

Treatment system 100 includes a treatment delivery device 110, treatment device movement actuator 112, patient support structure 120, support structure movement actuator 122, system base 130, real-time sensor system 140, and computer system 150.

The system base 130 is any one or more structures that serve as a base for mounting the other components of the system, and in various embodiments includes structural frames of any suitable material, as well as floors, walls and ceilings in a room in which the system is deployed.

Treatment delivery device 110 is any device used to deliver any therapeutic or diagnostic treatment to a particular site within a patient at the time the system is implemented, including a radiation source, such as that created by an accelerator with radiation field collimated with an aperture defining device, such as the multi-leaf collimator (MLC), a drill, a fluid injection system, an optical scope, and a biopsy needle, among others. The target site-specific nature of the treatment delivery device is indicated in FIG. 1 by the double-headed arrow 111a and arrow 111b, which are intended to converge at a target site in a patient. For example, in some embodiments, arrow 111a and arrow 111b represent radiation beams from two of multiple beam sources that converge to produce a lethal dose of radiation. In some embodiments, one arrow, e.g, arrow 111b, represents a physical probe and the other arrow, e.g., arrow 111a, is omitted.

Treatment device movement actuator 112 is any mechanism that serves to move at least a portion of the treatment delivery device 110. It is not intended to imply in FIG. 1 that every component of a multiple component treatment device is moved by actuator 112, only that at least a portion having to do with targeting a site is able to be moved by actuator 112 to keep on target. In some embodiments, the treatment delivery device 110 is stationary, and actuator 112 is omitted.

Patient support structure 120 is any component suitable for supporting or securing a patient in a vertical or horizontal position, including a board, a table, a stretcher, a chair, a gurney and a couch, among others.

Patient support structure movement actuator 122 is any mechanism that serves to move the patient support structure in one or more translational or rotational dimensions, or both. In some embodiments, the patient support structure 120 and actuator 122 are separate components. In some embodiments in which the support structure is stationary during treatment, actuator 122 is omitted.

In some embodiments, the structure 120 and actuator 122 are integrated. For example, in a prototype system, a robotic couch known as the HEXAPOD™ (Medical Intelligence, Germany) is integrated with multiple actuators capable of translational as well as rotational motion. The range of motion for the HEXAPOD couch is 3 cm in the medial-lateral directions (patient left to right directions) and cranio-caudal directions (patient head to toe directions), and 4 cm in the anterior-posterior directions (patient front to back directions) when the couch is at its central position. The range of rotational motion is 3° to pitch (head over heels), yaw (head left of heels) and roll (right over left) directions. Movement response times of the HEXAPOD are not suitable for compensating for patient breathing-induced motion of the target site, as explained in more detail below. Therefore, unlike the HEXAPOD, actuator 122 is configured with enough power to move patient support structure 120, when loaded by patient 190, sufficiently rapidly to compensate breathing-induced motion of the target tissue in at least one direction. In some embodiments, the actuator 122 is capable of moving the support structure 120 when loaded with a patient up to about 300 pounds. In some embodiments, lighter or heavier patients are accommodated.

Real-time state sensor system 140 is any device or system of devices used to determine a state of the patient that can serve as a non-invasive, real-time surrogate for movement of the target site. In some embodiments, the real-time state sensor system 140 is a set of two or more video sensors that detect the movement of the patient's outer surface (whether skin or clothing or other covering). In some embodiments, one or more markers that are easy to detect are placed on an outer surface of the patient. In some embodiments, other real time, non-invasive measurements appropriate for breathing are made. For example, one or more properties of air passing through the patient's mouth during breathing are measured by sensor system 140, such as volume, sound, velocity, humidity and temperature. In some embodiments, the expansion and contraction of the chest wall can be measured in real-time. Any of these properties of the patient that can be measured is called a state of the patient. The real-time state sensor system 140 makes real-time, non-invasive measurements of one or more states of the patient. Although shown in FIG. 1 as attached as an integral unit to base 130, in other embodiments the real-time state sensor system 140 includes one or more separated parts and can be placed anywhere appropriate out of the way of the treatment delivery device 110 and the movement of actuators 112, 122, or both FIG. 1 depicts the movement of a marker placed on an outer surface of a patient. At the first time when the patient cross section 191a and target site 193a are represented by solid perimeters, the marker is shown as triangle 142a with a solid perimeter. At the second time when the patient cross section 191b and target site 193b are represented by dashed perimeters, the marker is shown as triangle 142b with a dashed perimeter. In such embodiments, the real-time state sensor system 140 includes the marker whose position 142a, 143b are illustrated. In some embodiments a marker 148 is placed on or attached to patient support platform 120 so that positions 142a, 142b of one marker can be measured relative to the position of marker 148, such as embodiments in which the patient support structure 120 undergoes compensatory motion. In such embodiments, real-time state sensor system includes marker 148.

In an example embodiment, sensing of patient chest location was achieved with a DYNATRAC™ system (3DLine Medical Systems, Reston, Va.) consisting of three wall-mounted infra-red cameras interfaced into a control computer. Optical reflectors placed on the patient served as surrogate markers for tumor motion. The three-dimensional coordinates of the reflectors were computed using the three two-dimensional images of the reflectors captured by the three infra-red digital cameras, with a reconstruction algorithm. With more than 3 reflectors and continuous image capture, the translation and rotation of the patient was calculated from the changes in the reflector locations. In other embodiments, more or fewer cameras are used.

The system 100 also includes computer system 150. Computer system 150 comprises one or more general purpose or specific purpose processors with computer-readable media for storing information, as described in more detail in a later section. Computer system 150 is in communication with real-time state sensor system 140 and one or more actuators 112, 122 via corresponding direct communication links shown as thick lines in FIG. 1. In other embodiments, one or more of the communications links are replaced by indirect communications links, such as indirect communications through a network (including either or both local area networks and wide area networks). In some embodiments, one or more communication links are omitted.

The computer system 150 is configured to perform one or more processes used to determine movement compensation data to compensate for motion of the target site. In the illustrated embodiment, computer system 150 includes a partial least squares (PLS) process 152 and an internal model control (IMC) process 156, each described in more detail below with reference to FIG. 2 or FIG. 3. Instructions and data used by these processes are included on computer system 150 within the process boxes shown in FIG. 1. The PLS process 152 determines a patient-particular correlation between pre-treatment measurements of state from sensor system 140 and actual pre-treatment target site motion deduced from tomographic cross sectional images of the patient; and uses the correlation for computation of compensating movement data during treatment. The IMC process generates signals for at least one of the actuators 112, 122, based on known response properties of the device being moved, whether the device being moved is the patient support structure 120 or treatment delivery device 110.

In other embodiments, the computer system performs more or fewer or different processes, or some combination. For example, in some embodiments, a look-up table is created to relate the patient's state with the location of the target site. For example, a patient's breathing can be divided into 8 states, and the patient's images at these 8 states will reveal 8 locations of the target site. An example look up table follows.

TABLE

Example Look-up Table.

| | State | | | | | | | |
|---|---|---|---|---|---|---|---|---|
| | State 1 | State 2 | State 3 | State 4 | State 5 | State 6 | State 7 | State 8 |
| Location | $x_0$, $y_0$, $z_0$ | $x_1$, $y_1$, $z_1$ | $x_2$, $y_2$, $z_2$ | $x_3$, $y_3$, $z_3$ | $x_4$, $y_4$, $z_4$ | $x_5$, $y_5$, $z_5$ | $x_6$, $y_6$, $z_6$ | $x_7$, $y_7$, $z_7$ |

In this embodiment, the control computer system directs the couch actuator to move the patient support system such that the radiation beam is continuously aimed at the target site. The patient's images at different states are acquired with state of the art imaging devices. These include CT scanners, MRI, and fluoroscopy, ultrasound and optical imaging systems. When acquiring patient's images at different patient states, the images are "time-stamped" with the real-time measurement of the patient's state, so that each image is accurately associated with the state of the patient under which the images are acquired. For imaging modalities used in some embodiments, the state of the patient is contained in the images themselves. For example, when imaging the diaphragm region, the location of the diaphragm is in itself a measure of patient's breathing.

2. Pre-Treatment Modeling Overview

Figure 2:
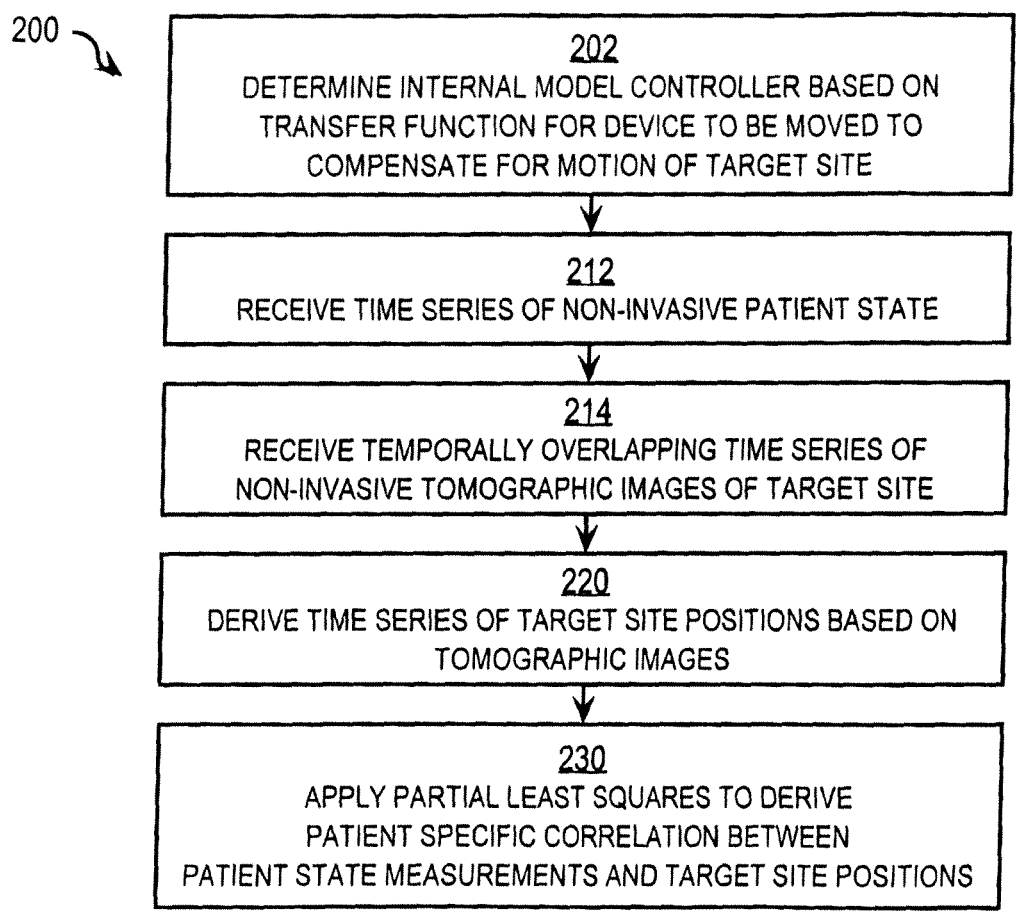
FIG. 2 is a flow diagram that illustrates at a high level a pre-treatment method for developing models used in the system of FIG. 1, according to an embodiment.

FIG. 2 is a flow diagram that illustrates at a high level a pre-treatment method 200 for developing models used in the system of FIG. 1, according to an embodiment. Although steps are shown in FIG. 2 and subsequent flow diagrams in a particular order for purposes of illustration, in other embodiments one or more steps are performed in a different order or overlapping in time, or performed in one or more parallel processes, or one or more steps are omitted, or the method is changed in some combination of ways.

In step 202, a model predictive control (MPC) system, such as an internal model controller (IMC), is developed to account for the temporal response of the device being moved when subjected to a command to move a certain amount. An MPC is a general name given to a control system that incorporates a process model prediction as part of a feedback control. In some embodiments, MPC schemes use optimization to invert a process model (such as the couch response function) with or without constraints. With IMC, the process model is inverted analytically, without eternal constraints. For example, in some embodiments, a treatment delivery device IMC is developed to account for response of the treatment delivery device when subjected to a command to move a certain amount sent to actuator 112. Similarly, in some embodiments, a patient support structure IMC is developed to account for response of the patient support structure when subjected to a command to move a certain amount sent to actuator 122.

As described in more detail below for a patient support platform and actuator in section 4.1, during development of an IMC, the temporal response of the device and actuator to an input is measured, is fit to an analytical function, and an inverted form of the analytic function is used to determine the size of the input for any desired result, within a range of valid inputs. In general, a device being moved a certain displacement has a response characterized by a dead time during which no movement occurs after receipt of a command to move, followed by an exponential change in position over time characterized by one or more time constants until the certain displacement is achieved as a steady state. This response is determined for each of the degrees of freedom in the driven motion of the device (e.g., up to three translational and up to three rotational degrees of freedom). The IMC uses these characteristics to form commands that are issued to the actuator during treatment delivery. These characteristics, once measured, are assumed constant for use by many patients. In some embodiments, these properties of the device movement are re-calibrated periodically. Thus step 202 is performed once for subsequent use during treatment delivery for many different patients.

The next steps are performed to establish a relationship between target site position and measurements of a surrogate signal based on real-time non-invasive measurements of patient state for a particular patient. For example, while an optical reflector placed on the skin provides a measure of the extent of motion exhibited by the external contour, the entity that is desired is a tumor as the target site. Compensation data is desired so that movement of the actuators negates the tumor trajectory, not the trajectory of the reflectors or other surrogate. For this reason, it is important to find a robust relationship between the "external" surrogate signal and the tumor trajectory. Initial studies by the inventors, as well as those of other investigators, have shown that there are phase lags between the respiration surrogate signal obtained from Real-Time Positioning (RPM) system (Varian Medical Systems, CA), which yields a 1-D amplitude and the position of the diaphragm. The steps to find this relationship, called herein a patient-specific correlation, involve pre-treatment steps 212, 214, 220, 230. In some embodiments, fiducial markers are invasively inserted at or sufficiently close to the tumor so that neither the surrogate signal nor the patient-specific correlation need to be determined In step 212, a time-series of measurements of patient state determined in real-time and non-invasively is received. Real-time measurements are measurements obtained in a time interval from starting the measurement to obtaining a value, which is negligibly short for purposes to which the measurements are applied. In the case of measuring a surrogate for tumor motion with periods of several seconds, a measurement made in a time short compared to a millisecond is considered a real-time measurement. Modern electronic devices are capable of hundreds of operations per microsecond; and measurements by such devices are considered real time. Non-invasive measurements are measurements that do not require cutting, piercing, bruising or causing pain to the patient. Patient state is any measurable property of the patient that serves as a surrogate for target site motion.

In the illustrated embodiment, the measurements received during step 212 are collected by the real-time state sensor system 140 to be used during treatment. In some embodiments, the measurements are made by a similar but separate system specifically for pre-treatment analysis. In an illustrated embodiment, the positions of optical reflectors are determined using the DYNATRAC™ system. This system is capable of handling up to 20 reflectors and uses 3 infra-red cameras. A reason for the choice of optical reflectors as tumor surrogates is that such reflectors are comfortable for patients and non-invasive. In addition, the use of optical reflectors allows for the use of multiple sensors on the patient at different locations on the torso, unlike many other sensors. As a consequence, instantaneous spatial coordinates corresponding to different parts of the external thoracic and abdominal anatomy can be obtained. While previous work has shown that there are phase and amplitude differences between the respiration cycle predicted by a single external marker placed on the abdomen of the patient and the motion of the internal anatomy, a quantitative predictive analysis of the correlation between multiple external markers and the tumor had been lacking. In preliminary work by the inventors, a high degree of correlation among multiple optical reflectors placed on the skin has been shown.

In an example embodiment, five reflectors were placed on the torso at the following locations, mid-sternum, xyphoid process, umbilicus, superior edge of inferior most rib on right side and inferior edge of inferior most rib on the left side. The positions of these reflectors were recorded for about 25 sec. The number of measurements in the time series was about 730 (sampling period of 33.33 ms×30 s duration) and the number of variables was 15 (5 reflectors×3 coordinates).

To determined target site, volumetric images obtained from computer tomography of various electromagnetic signals that pass through the patient's body are used. It is currently impossible to volumetrically image a tumor during treatment delivery.

In step 214, a time-series of non-invasive tomographic images of the target site are received that overlap in time the measurements received during step 212. The images are used to derive target site positions and are not used directly to form the patient-specific correlation. In other embodiments, other invasive or non-invasive measurements of the target site position are obtained instead of step 214. In some embodiments, volumetric tumor imaging is performed with four dimensional X-ray computed tomography (4D CT) imaging, well known in the art. In some embodiments, volumetric tumor imaging is performed with computer tomographic magnetic resonance imaging in a cinema mode that trades spatial resolution for rapid temporal scanning (cine MRI), also well known in the art. It is anticipated that, as future tomographic and other volumetric imaging systems are developed, some will be found suitable for use during step 214.

CT is still considered the "gold-standard" for lung and most abdominal imaging, particularly in radiation oncology. Further, the slice thickness of CT images is typically 3 millimeters (mm, 1 mm=$10^{-3}$ meters), or 1.5 mm for small lesions. The slice thickness of MR images is expected to be about 3 mm to about 5 mm. While 4D CT imaging is an active area of research and clinical implementation at this point, it has limitations for real-time applications. 4D CT imaging yields 8-10 3D CT data sets corresponding to the breathing cycle over an extended time period. When images are sorted according to phase (or amplitude) different slices in the volumetric data set corresponding to each phase (or amplitude) bin may correspond to different respiration patterns. 4D CT does not yield 3-D motion data corresponding to variations in respiration from one cycle to another. It simply yields an average tumor position as a function of an averaged respiration signal. Therefore, one has to assume that the average tumor trajectory is repeated from one respiration cycle to another. Such temporal resolution over an extended duration is considered inadequate if the object is to "chase" or compensate for motion of the tumor in real-time.

In some embodiments other types of tomographic images are used, such as tomographic images with better temporal resolution. Cine MRI allows for visualizing images of moving objects over time using magnetic resonance (MR) imaging. Essentially, multi-slice images are collected in a very rapid sequence of 100 to 200 milliseconds per image (ms/image, where 1 millisecond=$10^{-3}$ seconds). The images are displayed in a video clip fashion to visualize the motion. This modality, unlike 4D CT, accounts for variations in respiration patterns during a 10 minute to 30 minute duration typical of treatment delivery protocols.

In step 220, a time series of target site positions is derived based on the series of tomographic images received in step 214. In some embodiments, tumor positions from tomography are interpolated in time to resolve breath to breath variations based on other measurements, such as fluoroscopy imaging and beacon transponders that send a radio frequency (RF) signal to a detector (e.g., Calypso Medical Systems of Seattle, Wash.). The utility of a finely sampled target site trajectory arises from the fact that the larger the number of samples, the "richer" the data set and better the patient-specific correlation. In an illustrated embodiments, Cine MR images are contoured by a radiologist to determine the tumor volume, e.g. using a computer assisted tool such as the Pinnacle planning system from Phillips Medical Systems of Cleveland, Ohio. The tumor position is described by its center-of-mass (COM). In some embodiments, the tumor position is defined by a centroid of the tumor volume. Our preliminary studies with 4D CT images show that describing the tumor motion by its center of mass or centroid produces good results for radiation treatments in terms of therapeutic doses applied within the tumor and safe doses applied outside the tumor. These assessments were performed with three-dimensional (3D) conformal and IMRT plans when motion compensation is simulated using a treatment couch as a patient support platform. In other embodiments, one or more other measures of target site position different from the COM are used.

In step 230, partial least squares (PLS) are used to derive the patient-specific correlation between patient state and target site position. In other embodiments, other methods, such as multiple linear regression (MLR) are used to correlate patient state measurements to target site position.

PLS is an ideal tool for applications in which there are many variables that need to be used to predict one or more responses, i.e., there are measured variables ("inputs") that can be used to predict the responses of other variables ("responses"). PLS is well known in other disciplines and has found successful application in economics, chemometrics and medical imaging. While MLR can be used for similar applications, such methods can break down when the number of variables is large, and the variables are redundant, i.e., collinear. If MLR is used when the number of factors is large and greater than the number of observations the resulting model will fit the sampled data well but will fail to predict any new data well due to over-fitting. In such cases, even though the number of input variables is large there are probably only a few "latent factors" that account for most of the variation in the response(s). Methods like PLS are able to overcome this problem by performing the regression on a small number of orthogonal latent variables, which are linear combinations of the original variables. The underlying idea then of PLS is to extract these "latent factors" that account for much of the variation in the inputs and responses while predicting the responses well. PLS, as applied during step 230 for tumors as a target site and reflector positions as patient state, is described in more detail below in section 4.2.

3. Method of Treatment Delivery

Figure 3:
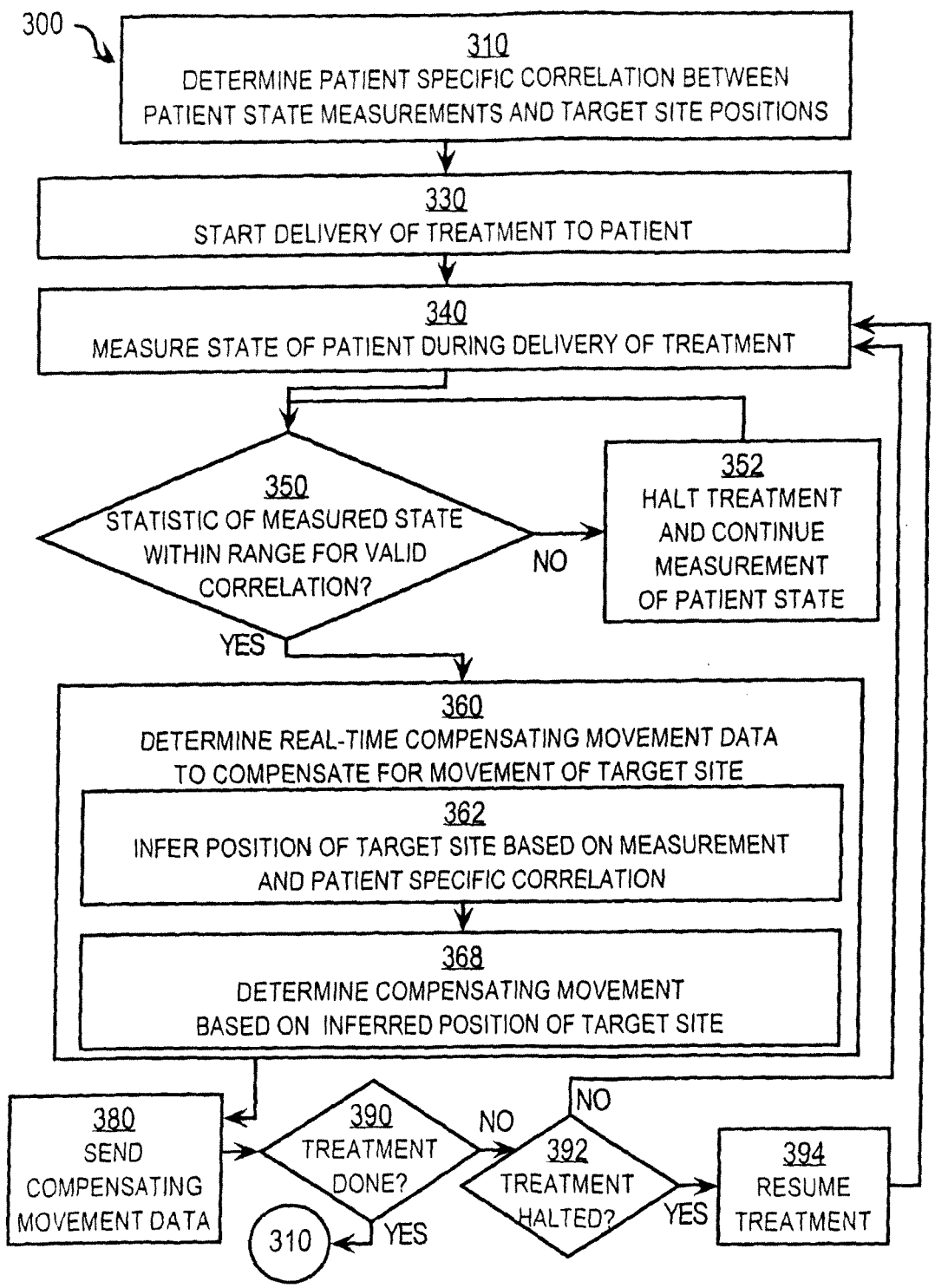
FIG. 3 is a flow diagram that illustrates at a high level a method for compensating for motion of a target site during treatment, according to an embodiment.

After the pre-treatment modeling, the system 100 is configured to treat a particular patient. A method to use system 100 to deliver treatment to a patient is described with reference to FIG. 3. FIG. 3 is a flow diagram that illustrates at a high level a method 300 for compensating for motion of a target site during treatment, according to an embodiment. For convenience, the term couch is used as shorthand for the patient support structure 120 in the following descriptions.

In step 310, a patient-specific correlation between patient state measurements and target site positions is determined Step 310 includes one or more of step 212, step 214, step 220, step 230, step 240 and step 248 of method 200, described above.

In step 330, delivery of treatment to the patient begins. Step 330 includes positioning the patient 190 on the couch 120 and placing one or more components of the real-time state sensor system on the patient, if any are to be so positioned. Step 330 also includes, determining the breathing pattern of the patient and determining the current real-time position of the target site. Either the treatment delivery device 110, or couch 120, or both, are moved until the target of the treatment delivery device coincides substantially with the current position of the target site. At that time, treatment delivery commences.

In step 340, non-invasive real-time measurements of patient state are made while treatment is being delivered to the patient. For example, measurements of positions 142a, 142b and others of a first reflector are made, along with measurements of positions of other reflectors, using the DYNATRAC™ system and a temporal sampling period of 33.33 ms.

In step 350, it is determined whether a statistic of the measured states indicates that the state data are in range for a valid correlation. Step 350 is designed as a safety measure for the patient, so that if a patient moves voluntarily or involuntarily (e.g., in response to a sneeze or cough or cramp) or if other system failure occurs, then treatment delivery can be halted. To prevent runaway positive feedback, in the couch feedback system for example, in various embodiments redundant hardware or fault detection algorithms, or both, are incorporated into the controller. If the controller in the feedback system tries to achieve a velocity and/or acceleration that exceed a specified limit, then the system can be shut down. An alternative embodiment uses a hardware-based interlock system such as an accelerometer to disable the system momentarily. For large tumor position errors, an interlock is designed shuts the radiation off momentarily until the errors are again within tolerance. In other embodiments, step 350 or analogous steps are moved to a different order or repeated after different steps, such as during step 368, described below. However, for the purposes of illustration, step 350 is performed as shown in FIG. 3A.

If it is determined in step 350 that the statistic is not within a range for valid correlation, then control passes to step 352. In step 352, treatment delivery is halted while measurements of patient state are continued. Any method may be used to halt treatment. Control passes back to step 350.

If it is determined in step 350 that the statistic is within a range for valid correlation, then control passes to step 360. In step 360, real-time compensating movement data is determined to compensate for detected movement of the target site. Any method may be used to determine the compensating movement data. In some embodiments with mechanical connections between measurement of patient state and movement of the couch or treatment delivery device, step 360 is omitted. In the illustrated embodiment, step 360 includes steps 362 and 368.

In step 362, the current position of the target site is inferred based on the measurement of patient state and the patient-specific correlation determined in step 310.

In step 368, the compensating movement data is determined based on the current and past inferred positions of the target site.

After step 360, control passes to step 380. In step 380, compensating movement data is sent to the actuator for the device being moved, e.g., the actuator 112 for the treatment delivery device, or the actuator 122 for the couch 120, or both. Control then passes to step 390.

In step 390, it is determined whether treatment delivery for the current patient is completed. If so, control passes back to step 310 to determine the patient-specific correlation for the next patient.

If it is determined in step 390 that treatment delivery for the current patient is not completed, then control passes to step 392. In step 392, it is determined whether treatment delivery for the current patient has been halted, e.g., in step 352 or in response to computing compensating movement data during step 360 that exceeds some threshold. If not, control passes back to step 340 to continue making measurements of patient state during treatment delivery. If it is determined in step 392 that treatment delivery for the current patient has been halted, then control passes to step 394 to resume delivering treatment based on the new movement data. Control then passes back to step 340 to continue making measurements of patient state during treatment delivery.

In step 362, the patient-specific correlation is used with a current real-time patient state measurement to obtain a current inferred position of target site. For example, the PLS model based on a tumor trajectory that was acquired during the pre-treatment cine MRI analysis is used to infer tumor position during treatment delivery. For real-time motion-synchronized couch-based treatment delivery it is desired that the correlation between surrogate breathing signals and tumor motion remain substantively unchanged. It has been shown that respiration waveforms are not entirely reproducible from one treatment to another, so some variability is expected. In some embodiments, the reproducibility of respiration patterns is improved through audio and visual coaching methods. In the illustrated embodiment, a particular patient-specific correlation is considered a success if the resulting inferred position of the center of mass (COM) is expected to be within 1 mm in the x, y and z directions, respectively, with a reasonable degree of certainty. This criterion is based on the fact that our preliminary results have shown that if the residual error is <4 mm, then the change in dose distribution is such that the decrease in tumor coverage (volume of the tumor receiving the prescription dose) is <3%. This is believed to be an acceptable criteria for residual measured dose (dosimetric) error.

In step 368, the compensating movement data is determined based on the past and current inferred positions of the target site and the IMC. Step 368 for an illustrated embodiment of the IMC is described in more detail below, in section 4.1.

4. Example Embodiments

The high level methods are described above, with reference to FIG. 2 and FIG. 3. In the following sections, more details are given for particular embodiments. In the detailed embodiments described in the following, the device being moved is the couch 120, and the target site is a tumor, such as a tumor in the lung or liver of a human patient, that moves with respiration by the patient.

The tumor position is a function only of the breathing when the treatment delivery device, e.g., a MLC or linear accelerator (linac) or CYBERKNIFE is moved to compensate. This constitutes an open-loop control system. The tumor position is a function of both the respiration and couch motion when the couch is moved, i.e., the compensatory action of the couch itself influences the tumor motion. The moving couch constitutes a closed-loop feedback system. An inherent advantage of a closed-loop feedback system is that it can by nature overcome uncertainty due to irregular breathing patterns. A closed-loop feedback system can be implemented safely by using interlock and over-rides that stop treatment (such as radiation therapy) if a violation of specifications occur, e.g., if movement exceeds some threshold.

A further advantage of a couch-based system is less complexity. It is assumed for purposes of illustration that in an open-loop control system using an MLC, the size of a tumor is about 7 cm to 8 cm in a direction perpendicular to the leaf travel direction and the beam direction. In this case, approximately 16-18 pairs of leaves are needed to provide compensation. Each leaf has its own control system, thereby requiring 32 to 36 control systems. In some embodiments of a couch-based system, compensation is applied in 3 directions, thereby requiring only 3 control systems. The couch-based system is therefore likely less complex.

Furthermore, acceleration and deceleration experiments performed with a state-of-the art MLC show "littering" as the MLC slows down, which could potentially affect the performance of the control system with the current MLC design.

Proof-of-principle experiments were performed with a commercial couch at a motion period of 16 s, about four times the normal respiration period. By using faster and more powerful actuators it is possible to design and build a couch that is fast enough to compensate for actual breathing-induced tumor motion, as described in more detail below. Radiation was delivered at a dose rate of 100 MU/minute, ¼th the normal clinical dose rate of 400 MU/min. Motion period and dose rate parameters were chosen that are similar to a clinically realistic intra-fraction motion period and a dose rate of 4 s and 400 MU/min, respectively. A "motion platform" that was driven by a mechanical sinusoidal oscillator was constructed. A phantom consisting of solid water blocks and measuring 16 cm in total thickness was placed on top of the platform. Film was placed at a depth 8 cm and sandwiched between solid water blocks. The platform was driven with a motion period of 16 s.

Proof of principle measurements were performed for three cases: (1) no phantom motion, (2) phantom motion with no couch tracking, and (3) phantom motion with couch tracking. The dynamic arc plan consisted of 9 segmented arcs that ranged from 30° to 50°. Planning was performed in the Ergo treatment planning system (3DLine Medical Systems, Reston, Va.). The total number of monitor units (MU) delivered using this plan were 434; and the delivery time including the loading of the fields at the treatment console was approximately 15 min. The dose per fraction was 2 Greys. We used a CLINAC 6/100 linear accelerator (Varian Medical Systems, Palo Alto, Calif.) fitted with a mini-MLC (3DLine Medical Systems, Reston, Va.) to deliver the above radiation beams. The mini-MLC is a tertiary collimator that fits into the head of an existing linear accelerator and the projected leaf-width at isocenter is 0.6 cm. The amplitude of motion was 1 cm and the type of radiation therapy (RT) delivery was dynamic conformal arcs. In each case, the area encompassed by the higher isodose lines decreased with phantom motion relative to the static case while the lower isodose lines expanded. When couch-based motion compensation is employed, the isodose lines agree to within 2 mm of the static case; indicating that the undesirable effects of 1 cm motion can be negated by compensating couch motion.

In the following, one or more characteristics of one or more components of a couch-based compensating movement system are described in more detail for other embodiments.

4.1 Model Predictive Control (MPC)

Here is presented an analysis of the dynamics for a prototype treatment couch and controller to compensate for respiration induced tumor motion. Model predictive control (MPC) controls a device, such as actuators for the couch or MLC, based on a model of the feedback system and device response. Any MPC method may be used. In an illustrated embodiment, an internal model controller (IMC) is used as an embodiment of MPC, as described in more detail below.

As a first step, the open-loop (no influence of the controller) step response of a HEXAPOD couch is evaluated. This is a standard method for evaluating the dynamics of a "plant" or "process", which in these embodiments is the couch. To simulate an open loop response, a communications delay of 10 seconds was introduced between the couch and the HEXAPOD controller (effectively eliminating the effect of the HEXAPOD controller). The assumption was that the couch would take much less than 10 s to achieve steady-state.

A phantom with 5 optical reflectors affixed to it was placed on the HEXAPOD. The phantom was displaced by a distance of ±0.25 cm, ±0.5 cm, ±1 cm, ±2 cm and ±3 cm in the superior-inferior (SI) direction, and ±0.25 cm, ±0.5 cm, ±1 cm, ±2 cm in the medial-lateral (M-L) and anterior-posterior (A-P) directions. The influence of gravity was also investigated through measurements obtained in the AP direction. Data were obtained under two conditions: (1) no load on the couch (except the phantom with optical reflectors, which weighs <5 lbs) and (2) a weight of 229 lbs in form of a volunteer on the table. The time at which the step was input was determined from the software and saved in a log file along with the step input response data.

The data were fit to first and second order with dead-time models show below. The solution to a first order with dead time system is given by $$P(t) = \begin{cases} 0 & t \leq \theta \\ \Delta y(1 - e^{-(t-\theta)/\tau}) & t > \theta \end{cases} \quad (1)$$

where, P(t) is the system output (actual couch displacement), $\Delta y$ is the magnitude of the step input (requested displacement) and it is also the final steady-state change, and $\theta$ is the dead time, i.e., the time it takes the system to begin to respond to a change in the input. The system gain in our experiments was approximately unity and therefore not shown. The solution to a second order with dead time system is given by $$P(t) = \begin{cases} 0 & t \leq \theta \\ \Delta x(1 + (\tau_1/(\tau_2 - \tau_1))e^{-(t-\theta)/\tau_1} - \\ (\tau_2/(\tau_2 - \tau_1))e^{-(t-\theta)/\tau_2}) & t > \theta \end{cases} \quad (2a)$$

for an over-damped system (damping coefficient $\zeta > 1$) in which two time constants $\tau_1$ and $\tau_2$ are defined as follows.

$$\tau_1 = \tau/(\zeta - \sqrt{\zeta^2 - 1}) \quad (2b)$$

and $$\tau_2 = \tau/(\zeta + \sqrt{\zeta^2 - 1}) \quad (2c)$$

When the system is critically damped, $\zeta = 1$, and the solution is given by Equation 3.

$$P(t) = \begin{cases} 0 & t \leq \theta \\ \Delta y(1 - (1 + (t - \theta)/\tau)e^{-(t-\theta)/\tau}) & t > \theta \end{cases} \quad (3)$$

And $$\tau 1 = \tau 2 = \tau.$$

FIG. 4A is a graph 401 that illustrates the measured response of an existing couch and first order model with dead time fit to the measurements, according to an embodiment. FIG. 4B is a graph 430 that illustrates the measured response of an existing couch and second order model with dead time fit to the measurements, according to an embodiment. In both graphs 401, 430 the horizontal axis 402 indicates time in seconds from an arbitrary start time and the vertical axis 404 indicates couch displacement in millimeters. The measured response of the HEXAPOD couch is represented by the open circles 410 in both graphs 401 and 430. A start movement order is issued at 11.9 seconds. The first order model with dead time fit is plotted as trace 420 in graph 401. The values of the dead time and time constant $\tau$ for the first order fit were 1.16 seconds and 0.8 seconds, respectively. The portion of trace 420 less than the dead time on graph 401 is indicated by the horizontal bar 422. At later times, the couch displacement is modeled with an exponential drop having a single time constant. The second order model with dead time fit is plotted as trace 440 in graph 430.

It is observed that the couch model is better described by the second order model, especially in the vicinity of the initial drop off, indicated by the horizontal bar 442 in graph 430.

For a step size of $\geq 1$ cm, the two time constants $\tau 1$ and $\tau 2$ are equal with a value of 0.55 seconds (s) for a step size of 1 centimeter (cm, 1 cm=$10^{-2}$ meters). This indicates that the couch system is critically damped for step responses of this magnitude. A critically damped or over-damped couch system is a desirable feature. An under-damped system will oscillate to get to steady state and is not considered acceptable for these application.

While a step size of <1 cm produces two unequal time constants $\tau 1$ and $\tau 2$, the sum of the time constants $\tau 1$ and $\tau 2$ was approximately equal as a function of step direction. For the small step changes, 0.25 cm, 0.5 cm, and 1 cm the first order time constants are roughly equal (0.75 s and 0.84 s). For the 2 cm and 3 cm step changes the time constants increase, indicating a slower response. This suggests that a velocity limit may be reached (due to a current limit on the electric motors) when large step changes are attempted and that the couch dynamics are linear up to 1 cm and non-linear for step inputs >1 cm. No difference was observed with and without the volunteer weight on the couch. The time constants as a function of the direction of translation of the couch were approximately equal suggesting that there is no effect of gravity on the open-loop response of the couch.

We attribute the velocity limit and non-linear step response of the couch to an electrical current limit in the motors used in the couch. A velocity limit is a nonlinear effect, and should be eliminated if an internal model controller as described in the proposal is to be used to control couch motion. To eliminate the velocity limit, faster and more powerful electric motors and actuators are used in embodiments that use a couch movement actuator.

Thus, the HEXAPOD couch is unsuitable for compensating for a full range of respiration-induced motion. Nonetheless, the HEXAPOD couch result indicates the shape if not the magnitude of the time response to be expected in any real couch 120 and actuator 122 system. The HEXAPOD results are used with control system simulations to demonstrate the improvement achieved with an IMC in the feedback for a treatment couch, and the dynamics of a couch that is suitable for compensating for respiration induced motion.

In this demonstration, it is assumed that a single infrared sensor (optical reflector) is attached to the patient's skin and provides a measure of the patient's respiration. Infrared marker displacement waveforms were obtained using the Varian RPM™ system during patient 4D CT simulation. The RPM™ system consists of a marker block containing two optical reflectors, an infrared camera that localizes the optical reflectors, and system software that converts the displacement of the reflectors into a respiration signal. While this demonstration only considers one dimension, the analysis is easily extended to three dimensions by those of ordinary skill.

Figure 5:
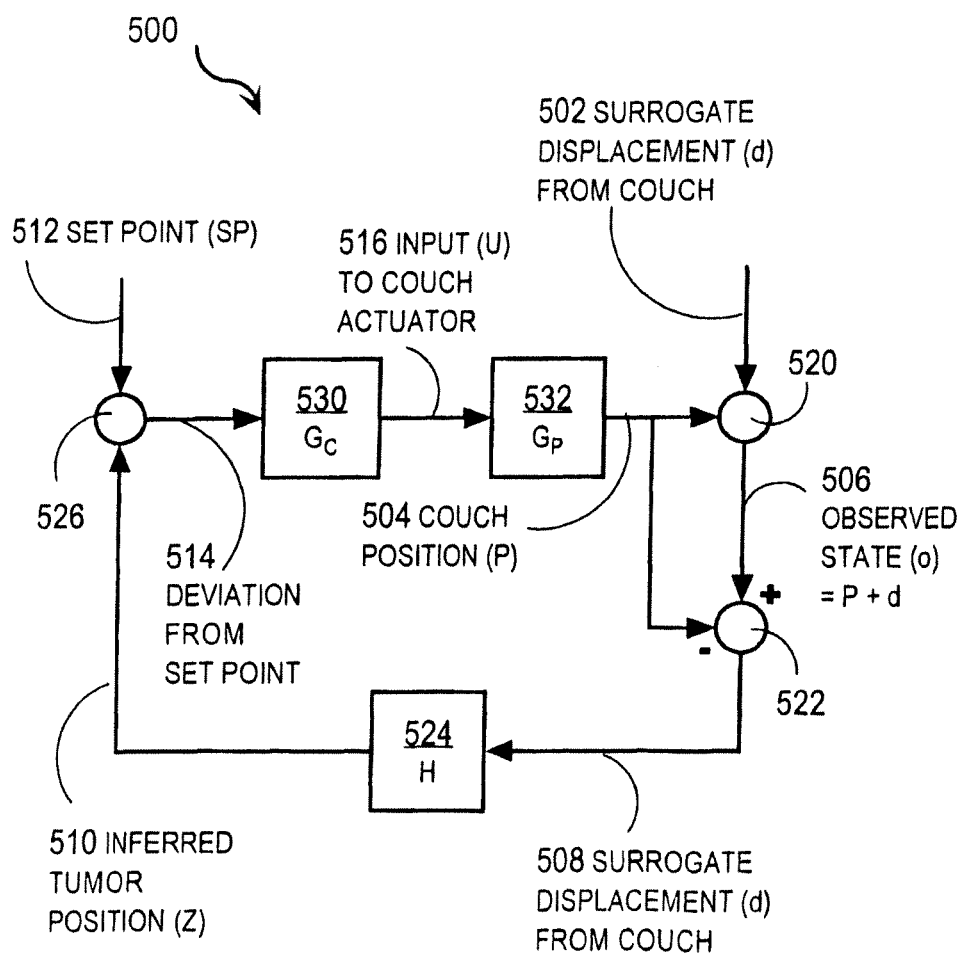
FIG. 5 is a block diagram that illustrates a simplified couch feedback control system, according to an embodiment.

FIG. 5 is a block diagram that illustrates a simplified couch feedback control system 500 according to an embodiment.

In FIG. 5, the control system 500 has six transfer function components that produce outputs based on inputs in a feedback loop. Inputs and outputs are indicated by arrows. A transfer function gives the relation between the input and output of a system. The six transfer function components include a reflector sensor system 520 that acts like an adder, a subtraction component 522, a correlator H 524, another subtraction component 526, a controller transfer function Gc 530, and a couch actuator transfer function Gp 532.

The reflector sensor system 520 responds to the couch position P 504 and the surrogate (reflector) displacement d 502 from the couch by providing an observed measurement of the state of the patient o 506 that represents the sum of the two inputs, i.e., o=P+d. In this embodiment the state of the patient is the position of the reflector in a geocentric reference frame. The position of the couch P 504 is also measured independently (for example with a reflector 148 on the couch 120) and input to subtraction component 522. Subtraction component 522 subtracts P from o to give d, the surrogate displacement from the couch d 508. It is noted that d 508 agrees with d 502 within the combined measurement errors of o and P. The correlator H, like the PLS patient-specific correlator described above, produces an inferred tumor position Z 510 based on the displacement d of the surrogate from the couch. The set point sp 512, where the tumor is desired to be stationary is known. The inferred position of the tumor is differenced from sp 512 in subtraction element 526 to yield a deviation 514 from the set point.

The controller transfer function Gc 530 determines an input u 516 for the couch actuator 122 based on the deviation 514 of the tumor position from the set point. The couch 120 and actuator 122 has a Gp 532 that is a transfer function that represents a consolidation of the couch actuator 122 and software dynamics. The output from Gp 532 in response to the input u is a new couch position P 504, thus completing the feedback loop.

In some embodiments, u 516 is set equal to the deviation 514 and Gc 50 is absent. According to preferred embodiments of the invention, the controller transfer function Gc 530 is selected to be an inverse of at least part of the couch actuator transfer function Gp 532. Such a controller transfer function Gc is called herein the internal model controller (IMC); it is a controller based on a model of the other components in the feedback loop.

The dynamic response of H was assumed to be very fast (microseconds) and therefore was considered as a pure gain for this embodiment. The value of the gain of H was set to 1, i.e., it was assumed for purposes of illustration that there is a one-to-one correspondence between the infrared sensor position and the tumor position. The exact value of the gain of H does not change the analysis given here since a non-unity gain can be compensated in the controller. The transfer functions Gp for a first and second order couch systems are given in Equation 4 and Equation 5, respectively.

$$G_p = \frac{e^{-\theta s}}{\tau s + 1} \quad (4)$$

$$G_p = \frac{e^{-\theta s}}{\tau^2 s^2 + 2\zeta\tau s + 1} \quad (5)$$

Where s is the Laplace transform variable with units of inverse seconds, related to time t by the Laplace transform, well known in signal processing.

The couch-based motion compensation system is a closed-loop system, i.e., any compensatory action on the part of the couch affects the position of the infrared sensor itself. Therefore, feedback control prefers that any change in couch position be subtracted out of the measurement. If the couch position is not subtracted out then an inaccurate estimate of the tumor position results. The tumor moves due to a breathing disturbance d related to movement of the surrogate with respect to the couch. The desired value of the tumor position is sp=0, since the goal of the control system is to keep the tumor stationery. The couch position is measured by a second infrared sensor and it is given by P. It is noted that in most control systems only the measurement of the output state, o, which is affected by both the disturbance d as well as the process dynamics Gp is typically available. The fact that in this system couch position P can be measured separately allows for an internal model control system based on the disturbance d to be used.

In an internal model control (IMC) system, the controller used involves the inverse of the invertible part of the dynamics of the process Gp to be controlled. The block diagram in FIG. 5 is that of an internal model controller (IMC) with a perfect process model Gp. If the controller Gc were also perfect, for H=1 the following controller transfer function would be used.

$$G_c = 1/G_p^+ \quad (6)$$

Since a dead time cannot be inverted, $G_p^+$ will only contain time constant terms. It can be noted that if the dead time θ=0 then an internal model controller with a perfect controller model would achieve perfect control of y. For a first order process Gp, the controller transfer function is $$G_c = (\tau s + 1) \quad (7)$$

and for a second order process Gp, the controller transfer function is given by Equation 10a, below.

In some embodiments, a robustness filter is used in the control system. By adding a robustness filter the control system shown in FIG. 5 can be tuned to insure closed loop stability. In the absence of such a filter, the controller has a tendency to amplify the higher frequency noise as well as errors between the controller model and actual actuator performances. In an embodiment, a filter with a time constant of 0.1 times the controller time constant (this is based on a general rule of thumb in process control) is introduced. The transfer function for controller with the robustness filter (one-tenth the size of the controller time constant) is shown in Equation 8, where $\tau_f = 0.1\tau$.

$$G_c = \frac{(\tau s + 1)}{(\tau_f s + 1)} \quad (8)$$

Simulations were performed by varying the time constants associated with the couch dynamics and control system and the system dead time. The dynamic constants were reduced by the same factor of 0.1, e.g. all time constants were shrunk by the same factor starting with values exhibited by the HEXAPOD™ couch to 0.068 s for the time constant and 0.067 s for the dead time. The control system was simulated and solved using an analytical solution, which employs partial fraction expansion.

Figure 6A:
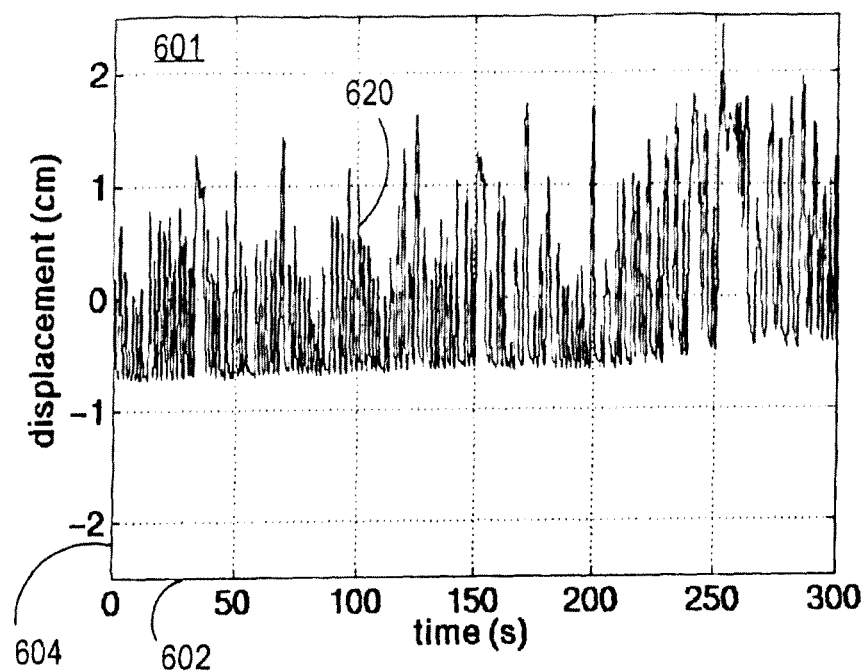
FIG. 6A is a graph that illustrates the one dimensional measured displacement of a tumor.
Figure 6B:
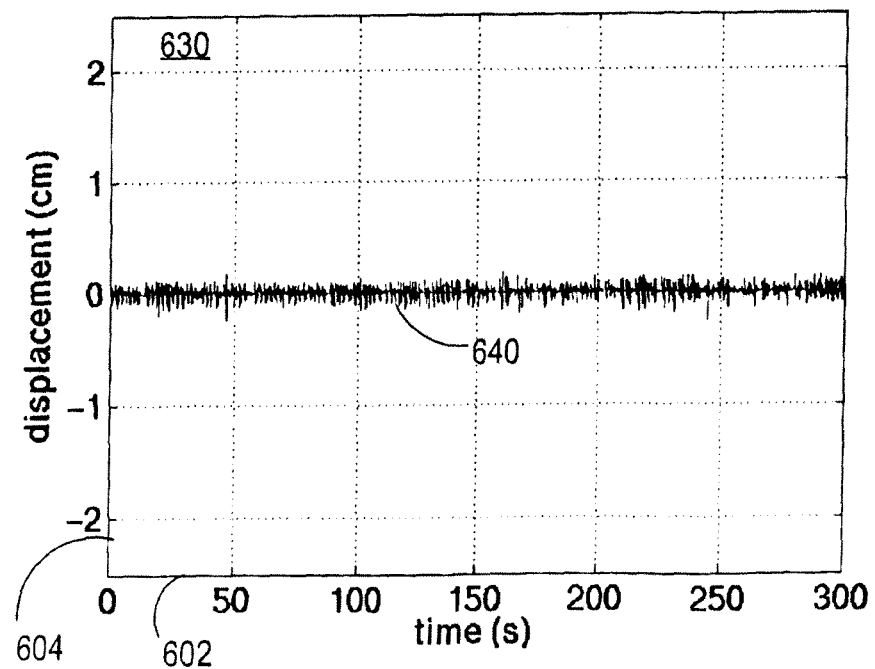
FIG. 6B is a graph that illustrates the residual tumor motion after feedback control using an internal model control (IMC) system, according to an embodiment.

A detailed analysis has been performed for 1-D tumor surrogate displacement obtained from 12 patients. In this analysis, the tumor surrogate motion was considered equal to the tumor motion. FIG. 6A is a graph 601 that illustrates the one dimensional measured displacement of a tumor. FIG. 6B is a graph 630 that illustrates the residual tumor motion after feedback control using an internal model control (IMC) system, according to an embodiment. In both graphs 601, 630 the horizontal axis 602 indicates time in seconds and the vertical axis 604 indicates tumor displacement in centimeters. The tumor displacement on a couch at rest is plotted as trace 620 in graph 601. The residual tumor displacement on a couch with compensating movement based on feedback control using an IMC system is plotted as trace 640 in graph 630.

For the data in FIG. 6A and FIG. 6B, the couch dynamics Gp are described by a second order system with 2 equal time constants ($\tau_1 = \tau_2 = 0.068$ s), the control system Gc is described by a first order system with a time constant of 0.10 s and the dead time of the couch is 0.067 s. One-dimensional tumor motion data obtained over a 5 min duration for a representative patient show tumor displacements as high as 1.5 cm. Residual tumor motion after feedback control using the internal model control system show tumor displacements that are less than 0.3 cm.

The adequacy of this performance is evaluated by calculating the sum of the absolute value of the tumor displacement and the number of sampled displacements greater than 0.3 cm. Both calculations were normalized to the number of sampled displacement points. The results indicate that it is possible to obtain a residual tumor motion of <0.3 cm for all 12 patients with couch-based tumor motion compensation for input motion amplitudes of 1.5 to 2 cm when the couch time constants and dead time are both <100 ms.

Part of the dead time in the HEXAPOD couch is due to the slow data rate at the interface that receives the commands to move and the slow speed of the internal processor. With modern computers operating at greater than 2.5 GigaHertz (GHz, 1 GHz=$10^9$ cycles per second) and Ethernet connections of 100 Megabits per second (Mb/s, 1 Mb=$10^6$ binary digits), the processing bottleneck of the HEXAPOD couch is essentially eliminated in some embodiments.

It is noted that a single "spike" was observed for the residual displacement even with an IMC and couch having the desired dynamics for one patient among a group of 12 whose breathing was monitored. If such a "spike" in residual tumor displacement is deemed unacceptable for patient safety, the radiation beam can be momentarily turned off and resumed when the residual displacement is acceptable.

Note that in some embodiments, motion in two or three dimensions is controlled. In some of these embodiments, there are three control systems used, one each for x, y and z directions, and each of these control systems have the block diagram shown in FIG. 5.

The results are used to specify the dynamic behavior of a couch specifically designed to compensate for tumor motion during breathing. Equation 3 for a critically damped system gives the couch transfer function that produces these control results. To design a couch using this transfer function one specifies the maximum excursion of a tumor in each spatial direction. If it is assumed that the maximum excursion is 3 cm, the maximum transient velocity is calculated by differentiating Equation 3a for the critically damped case, which yields the couch velocity for the critically damped case.

$$P'(t) = \Delta y \left( \frac{te^{-(t-\theta)/\tau}}{\tau^2} - \frac{\theta e^{-(t-\theta)/\tau}}{\tau^2} \right) \tag{9}$$

It can be shown that the couch velocity is maximum when $t=\tau+\theta$ and the maximum value is $\Delta y e^{-1}/\tau$. For $\tau=0.068$ s, and $\Delta y=3$ cm, the maximum velocity is 16.2 cm/s. Thus, the couch electric motors and actuators are designed to achieve this velocity. They are also designed so that the transient response remains linear at velocities equal to or less than this maximum. At couch velocities up to 16.2 cm/sec no velocity limit occurs, e.g. there is electrical current limitation. It is anticipated that the couch design includes a safety factor to the design, e.g. the couch is designed for a maximum velocity of 18 cm/sec. Since the 0.068 s value for $\tau$ is approximately 8 times faster than the value of $\tau$ for the current couch (assuming a second order with dead time model), namely 0.54 s, the motors and actuators for a couch according to some embodiments responds at least eight times faster than those in the current couch. However, the current couch exhibits a velocity limit for step changes greater 1 cm. For 3 cm step changes the required couch velocity is increased by another factor of 3, since P' is proportional to $\Delta y$. Thus, motors and actuators that are approximately 24 times faster than the HEXAPOD couch are used. If it is assumed that response speed and motor power are correlated, then a 24-fold increase in speed involves a 24-fold increase in power.

Actuators with such power and speeds are well within the capabilities of current technology, and well known in the art. See, for example, ALN002BI18 series motors from DYNETIC SYSTEMS of Elk River, Minn., and MDRIVE34™ motors from INTELLIGENT MOTION SYSTEMS, INC. of Marlborough, Conn. It is noted in particular that the ALN002BIi8 motor has time constants less than 5 ms, as desired for a couch to respond to breathing movements.

The power capacity of available motors is shown as follows. Power=VI where V is the voltage and I is the current. Current specifications for one of the DYNETIC models specifies maximum voltage and current. Therefore, maximum Power=24×114=2.7 kiloWatts (kW, 1 kW=$10^3$ Watts). The maximum power needed for a couch compensating for patient breathing may be approximately calculated as follows. It is assumed for purposes of illustration that a 300 lb patient (136 kg) is supported on a suitable couch (~60 kg). Using Equation 9, the acceleration may be determined by taking the derivative of the velocity. The maximum acceleration is determined to be 0.88 m/s². Using Newton's law, F=ma where F is the force, m is the mass and a is the acceleration, F=196 kg×0.88 m/s²=173 Newtons. Power=Force×velocity, so the required Power=173 N×0.18 m/s=31 W. Thus the 2.7 kW available from the DYNETIC motor is well in excess of the 0.031 kW needed to move patient and couch.

In various other embodiments, a higher order controller response function is used, given by Equation 10a for a second order response, and by Equation 10b for a second order response with a robustness filter term $\lambda=\tau f$ added.

$$G_c = (\tau_1 s + 1)(\tau_2 s + 1) \tag{10a}$$

$$G_c = \frac{(\tau_1 s + 1)(\tau_2 s + 1)}{(\lambda s + 1)^2} \tag{10b}$$

4.2 PLS Modeling

Partial Least Squares (PLS) modeling is used to infer target site position based on real-time non-invasive measurements of patient state, as described above. That is, a PLS model is used within transfer function H 524 in system 500 depicted in FIG. 5. The PLS modeling for generic systems is described, for example, in Wold S, Ruhe A, Wold H, Dunn W J III, The collinearity problem in linear regression. The Partial Least Square approach to generalized inverses, *SIAM J Sice Stat Compute* vol. 5, 735-743, 1994., the entire contents of which are hereby incorporated by reference as if fully set forth herein. In the embodiment described in this section, patient state is the position of one or more reflectors on the patient's skin, and the target site is a tumor centroid determined from 4D CT and cine MRI.

Consider a matrix X (predictor matrix) that contains m observations and n variables and a matrix Y (response matrix), which has m responses and r variables. At each stage, PLS calculates two latent variables: tj, a linear combination of the original X matrix variables and uj a linear combination of the Y variables. These variables are chosen such that the covariance between tj and uj is maximized. The algorithm can be briefly stated as follows. The variable u is set equal to a column of Y A weight matrix w is then calculated by regressing the columns of X on u. Then, w is normalized to unit length. The score matrix t is calculated as $t=Xw/w^T w$. A loading matrix q is then calculated as $q^T=t_T Y/t^T t$ by regressing the columns of Y on t. A new u vector is then calculated as $u=Yq/q^T q$. The convergence is then checked for u, e.g., convergence is obtained when the difference between successive versions of u is tolerably small, i.e., less than some predefined tolerance. If convergence is determined, then the loading matrix p is calculated as $p=X^T t/t^T t$. If convergence is not determined, then the process is repeated starting with the calculation of the weight matrix w. If convergence is determined, then a residual matrix is calculated as $E=X-tp^T$ and $F=Y-tq^T$.

If additional PLS dimensions are necessary, then the X and Y matrices are replaced by E and F and the process I repeated for th other dimensions. The number of PLS dimensions required to predict the responses well and not over-fit the data is determined by cross-validation. During cross-validation, the reference data set is divided into subsets and a new PLS model is generated using all but one of the subsets. The model is then used to predict Y and the prediction error sum of squares (PRESS) for this subset is calculated. This procedure is repeated until all of the subsets have been deleted once. The PRESS values for each subset are summed to obtain an overall PRESS.

The PLS-based model in this embodiment is applied to two components: (1) reflector positions from the DYNATRAC™ software (X), and (2) spatial position of the tumor from cine MRI data (Y). Note that the terms optical reflectors and markers are used interchangeably herein. The reproducibility of the positioning of the optical reflectors has been determined to be <0.3 mm. The camera system includes 3 infra-red cameras installed in the MRI suite. The time clocks of the infra-red camera system are synchronized with that of the MR scanner. This ensures a temporally synchronized mapping of the time dependent spatial coordinates of the optical reflectors and the tumor. In an illustrated embodiment, eleven reflectors are placed at the following locations directly on the patient's skin. In other embodiments more or fewer reflectors are placed on the patient's skin. The markers are placed at the sternal notch, mid-sternum, xyphoid process, 5 cm lateral to each nipple, with 3 markers along the inferior most aspect of the rib cage bilaterally starting 7 cm from the xyphoid process and spaced every 7 cm. The locations of these points range from the upper thorax to the upper abdomen and are selected in a relatively stable part of the anatomy. For example, reflectors could be placed near the umbilicus; but patients often lose weight during RT and likelihood of weight loss being manifested near the umbilicus is high.

Patients are scanned such that the immobilization and anatomical positioning mimics the patient positioning during treatment as closely as possible. This is to ensure that the PLS model developed at the time of MR imaging, pre-treatment, is valid during treatment delivery. In various embodiments, two immobilization devices are used: (1) a mesh body cast, which is rigidly attached to a "base-plate" that is securely fastened to the imaging or treatment table (3DLine Medical Systems, Milan, Italy) and (2) a body fix device that utilizes a vacuum suctioned air bag (Medical Intelligence, Germany). Parts of these devices are duplicated to be MR compatible during the MR imaging process. These immobilization devices are modified to allow for the placement of reflectors directly on the patient's skin. In some embodiments, circular tape with a female screw thread is placed on the skin and the optical reflector with male screw threads screws into the female thread. The immobilization device is then placed over the reflectors. In other embodiments, small holes are cut into the immobilization device at the desired anatomical location and the reflectors are placed directly on the exposed skin using circular tape.

An important difference between pre-treatment and treatment delivery conditions is that the couch does not move during pre-treatment when cine MR imaging is performed, while the couch is designed to move during treatment delivery in some embodiments. Hence, during treatment delivery, the instantaneous positions of the reflectors include the displacement of the patient skin not only due to respiration but also due to the motion of the treatment couch. In order to extract the displacement of the couch and determine the displacement of the optical reflectors due to normal respiration solely, at least one reflector (e.g., marker 148) is placed directly on the couch to register couch motion independently. Then the position of the reference marker can be subtracted from the 11 markers. The difference between the coordinates of the 11 markers and the reference marker reveals the surrogate signal for the tumor displacement due to respiration alone. No such subtraction is performed during MR imaging.

In this embodiment, the PLS model is implemented using the PLS toolbox from EIGENVECTOR TECHNOLOGIES™ (Eigenvector Research, Inc., Manson, Wash.) for MATLAB™ (Mathworks Inc, MA). Once the PLS model is fully developed and tested, the MATLAB code is converted into C-language code for real-time implementation.

In this embodiment of the PLS model, the X matrix consist of the x, y and z coordinates of the 11 reflectors placed as described above and determined by the camera system. Therefore the number of variables is 33 (11×3). The sampling period of the camera is 33 ms. For a 5 min scan, that yields approximately 9100 observations. At the same time, cine MR images of the tumor are obtained with a temporal period of 0.5 s. Therefore, for a 5 min duration, approximately 600 tumor locations are obtained. In the PLS model building process, only those positions of the reflectors that have corresponding tumor images are used. As a result, only approximately 600 recorded reflector and tumor coordinates are used in the PLS model development.

The X matrix therefore has dimensions of 600×11. The response matrix Y becomes a 600×3 matrix corresponding to the tumor locations (defined by the tumor centroid).

In the case of lung tumors, the phenomena of hysteresis is widely known. This means that for the same locations of the markers, the tumor position may be different depending on whether the patient is inhaling or exhaling. Therefore, two PLS models are built—one for the inhalation portion of the breathing cycle and one for the exhalation. For a given optical reflector position, the software will first determine whether the patient is inhaling or exhaling. Then the appropriate PLS model is selected to infer the location of the tumor.

This work produces a regression matrix (or vector) based on the predictor matrix X and the response matrix Y Its use is in the prediction or inference of a future y (e.g., inferred tumor position z) given a new vector of the optical reflector coordinates. We assume that $x^T$ is a new vector of optical reflector coordinates obtained during treatment delivery. Inferred values of the response variables, e.g., the tumor centroid location z in FIG. 5, is obtained from the PLS latent vector form of the model as follows. The scores (T matrix) for each PLS dimension (a=1, 2, 3, ..., A) are calculated as $$t_a = e_{a-1} w_a / w_a^T w_a \qquad (11a)$$

and $$e_a^T = e_{a-1}^T - t_a p_a^T \qquad (11b)$$

The new inferred tumor position (z in FIG. 5) is then calculated as $$\hat{y} = \sum_{a=1}^{A} t_a q_a^T \quad (11c)$$

5. Computer System Overview

Figure 7:
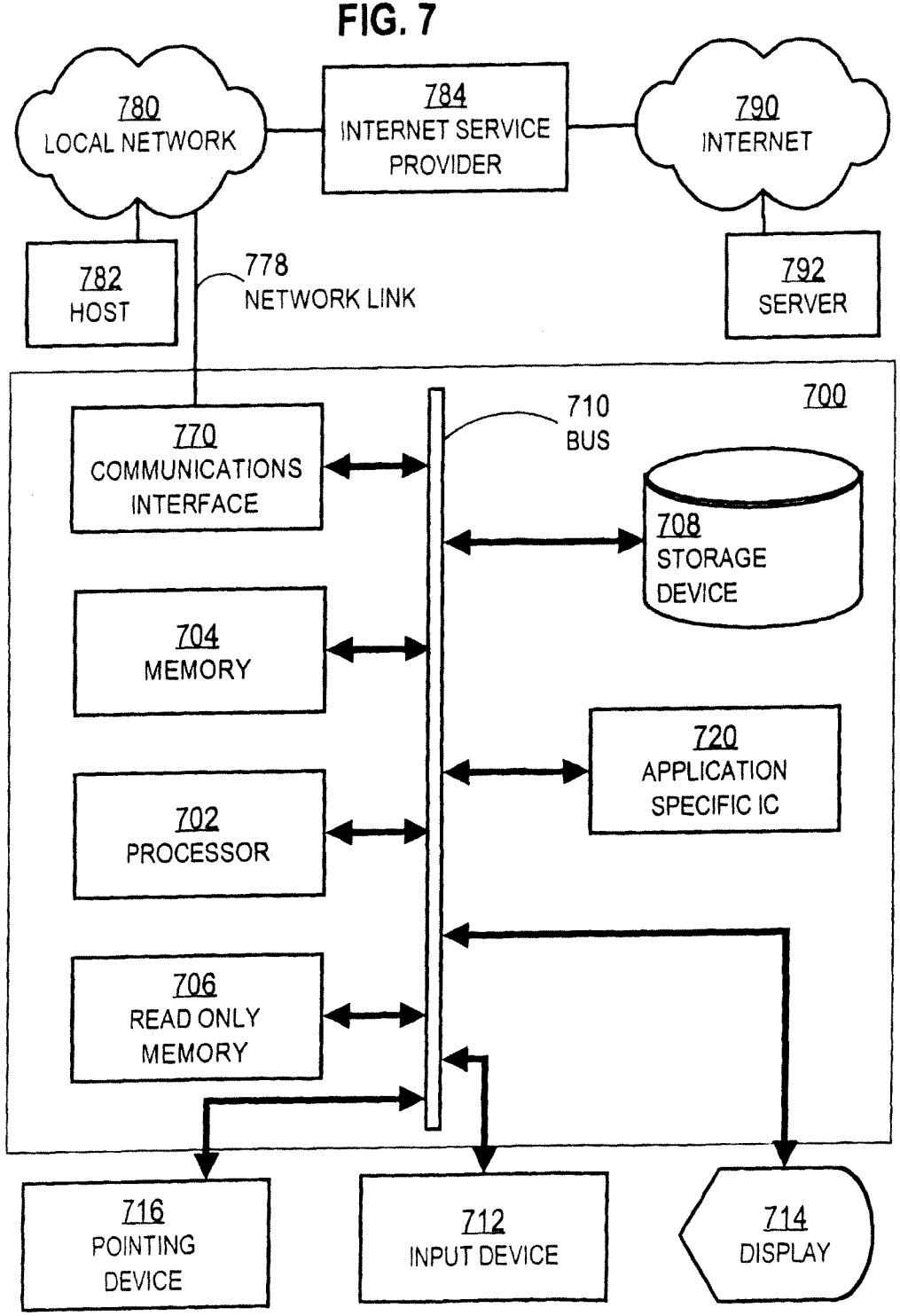
FIG. 7 is a block diagram that illustrates a computer system upon which an embodiment of the invention may be implemented.

FIG. 7 is a block diagram that illustrates a computer system 700 upon which an embodiment of the invention may be implemented. Computer system 700 includes a communication mechanism such as a bus 710 for passing information between other internal and external components of the computer system 700. Information is represented as physical signals of a measurable phenomenon, typically electric voltages, but including, in other embodiments, such phenomena as magnetic, electromagnetic, pressure, chemical, molecular atomic and quantum interactions. For example, north and south magnetic fields, or a zero and non-zero electric voltage, represent two states (0, 1) of a binary digit (bit). A sequence of binary digits constitutes digital data that is used to represent a number or code for a character. A bus 710 includes many parallel conductors of information so that information is transferred quickly among devices coupled to the bus 710. One or more processors 702 for processing information are coupled with the bus 710. A processor 702 performs a set of operations on information. The set of operations include bringing information in from the bus 710 and placing information on the bus 710. The set of operations also typically include comparing two or more units of information, shifting positions of units of information, and combining two or more units of information, such as by addition or multiplication. A sequence of operations to be executed by the processor 702 constitute computer instructions.

Computer system 700 also includes a memory 704 coupled to bus 710. The memory 704, such as a random access memory (RAM) or other dynamic storage device, stores information including computer instructions. Dynamic memory allows information stored therein to be changed by the computer system 700. RAM allows a unit of information stored at a location called a memory address to be stored and retrieved independently of information at neighboring addresses. The memory 704 is also used by the processor 702 to store temporary values during execution of computer instructions. The computer system 700 also includes a read only memory (ROM) 706 or other static storage device coupled to the bus 710 for storing static information, including instructions, that is not changed by the computer system 700. Also coupled to bus 710 is a non-volatile (persistent) storage device 708, such as a magnetic disk or optical disk, for storing information, including instructions, that persists even when the computer system 700 is turned off or otherwise loses power.

Information, including instructions, is provided to the bus 710 for use by the processor from an external input device 712, such as a keyboard containing alphanumeric keys operated by a human user, or a sensor. A sensor detects conditions in its vicinity and transforms those detections into signals compatible with the signals used to represent information in computer system 700. Other external devices coupled to bus 710, used primarily for interacting with humans, include a display device 714, such as a cathode ray tube (CRT) or a liquid crystal display (LCD), for presenting images, and a pointing device 716, such as a mouse or a trackball or cursor direction keys, for controlling a position of a small cursor image presented on the display 714 and issuing commands associated with graphical elements presented on the display 714.

In the illustrated embodiment, special purpose hardware, such as an application specific integrated circuit (IC) 720, is coupled to bus 710. The special purpose hardware is configured to perform operations not performed by processor 702 quickly enough for special purposes. Examples of application specific ICs include graphics accelerator cards for generating images for display 714, cryptographic boards for encrypting and decrypting messages sent over a network, speech recognition, and interfaces to special external devices, such as robotic arms and medical scanning equipment that repeatedly perform some complex sequence of operations that are more efficiently implemented in hardware.

Computer system 700 also includes one or more instances of a communications interface 770 coupled to bus 710. Communication interface 770 provides a two-way communication coupling to a variety of external devices that operate with their own processors, such as printers, scanners and external disks. In general the coupling is with a network link 778 that is connected to a local network 780 to which a variety of external devices with their own processors are connected. For example, communication interface 770 may be a parallel port or a serial port or a universal serial bus (USB) port on a personal computer. In some embodiments, communications interface 770 is an integrated services digital network (ISDN) card or a digital subscriber line (DSL) card or a telephone modem that provides an information communication connection to a corresponding type of telephone line. In some embodiments, a communication interface 770 is a cable modem that converts signals on bus 710 into signals for a communication connection over a coaxial cable or into optical signals for a communication connection over a fiber optic cable. As another example, communications interface 770 may be a local area network (LAN) card to provide a data communication connection to a compatible LAN, such as Ethernet. Wireless links may also be implemented. For wireless links, the communications interface 770 sends and receives electrical, acoustic or electromagnetic signals, including infrared and optical signals, that carry information streams, such as digital data. Such signals are examples of carrier waves.

The term computer-readable medium is used herein to refer to any medium that participates in providing information to processor 702, including instructions for execution. Such a medium may take many forms, including, but not limited to, non-volatile media, volatile media and transmission media. Non-volatile media include, for example, optical or magnetic disks, such as storage device 708. Volatile media include, for example, dynamic memory 704. Transmission media include, for example, coaxial cables, copper wire, fiber optic cables, and waves that travel through space without wires or cables, such as acoustic waves and electromagnetic waves, including radio, optical and infrared waves. Signals that are transmitted over transmission media are herein called carrier waves.

Common forms of computer-readable media include, for example, a floppy disk, a flexible disk, a hard disk, a magnetic tape, or any other magnetic medium, a compact disk ROM (CD-ROM), a digital video disk (DVD) or any other optical medium, punch cards, paper tape, or any other physical medium with patterns of holes, a RAM, a programmable ROM (PROM), an erasable PROM (EPROM), a FLASH- EPROM, or any other memory chip or cartridge, a carrier wave, or any other medium from which a computer can read.

Network link 778 typically provides information communication through one or more networks to other devices that use or process the information. For example, network link 778 may provide a connection through local network 780 to a host computer 782 or to equipment 784 operated by an Internet Service Provider (ISP). ISP equipment 784 in turn provides data communication services through the public, world-wide packet-switching communication network of networks now commonly referred to as the Internet 790. A computer called a server 792 connected to the Internet provides a service in response to information received over the Internet. For example, server 792 provides information representing video data for presentation at display 714.

The invention is related to the use of computer system 700 for implementing the techniques described herein. According to one embodiment of the invention, those techniques are performed by computer system 700 in response to processor 702 executing one or more sequences of one or more instructions contained in memory 704. Such instructions, also called software and program code, may be read into memory 704 from another computer-readable medium such as storage device 708. Execution of the sequences of instructions contained in memory 704 causes processor 702 to perform the method steps described herein. In alternative embodiments, hardware, such as application specific integrated circuit 720, may be used in place of or in combination with software to implement the invention. Thus, embodiments of the invention are not limited to any specific combination of hardware and software.

The signals transmitted over network link 778 and other networks through communications interface 770, which carry information to and from computer system 700, are exemplary forms of carrier waves. Computer system 700 can send and receive information, including program code, through the networks 780, 790 among others, through network link 778 and communications interface 770. In an example using the Internet 790, a server 792 transmits program code for a particular application, requested by a message sent from computer 700, through Internet 790, ISP equipment 784, local network 780 and communications interface 770. The received code may be executed by processor 702 as it is received, or may be stored in storage device 708 or other non-volatile storage for later execution, or both. In this manner, computer system 700 may obtain application program code in the form of a carrier wave.

Various forms of computer readable media may be involved in carrying one or more sequence of instructions or data or both to processor 702 for execution. For example, instructions and data may initially be carried on a magnetic disk of a remote computer such as host 782. The remote computer loads the instructions and data into its dynamic memory and sends the instructions and data over a telephone line using a modem. A modem local to the computer system 700 receives the instructions and data on a telephone line and uses an infra-red transmitter to convert the instructions and data to an infra-red signal, a carrier wave serving as the network link 778. An infrared detector serving as communications interface 770 receives the instructions and data carried in the infrared signal and places information representing the instructions and data onto bus 710. Bus 710 carries the information to memory 704 from which processor 702 retrieves and executes the instructions using some of the data sent with the instructions. The instructions and data received in memory 704 may optionally be stored on storage device 708, either before or after execution by the processor 702.

6. Predicting Position of Internal Anatomy Using Surrogates

Natural biometrical processes inevitably cause motion of a target. For example, as indicated above, tumors in the thorax and abdomen move during normal respiration. As a result, during radiation therapy, geometric misses of the target may occur resulting in under-dosing of the target or radiating the surrounding healthy tissue. Embodiments of the invention are able to determine the position of the internal anatomy (e.g., tumor) indirectly but accurately using surrogates placed on the skin of the patient without invasively measuring the position of the tumor (e.g., using implanted fiducials). Thus, embodiments of the invention eliminate the need for continuous monitoring of the anatomical position by monitoring the position of implanted fiducials or continuously imaging (x-ray) the patient during treatment, thereby reducing the level of unnecessary radiation.

Anatomical motion is critical to radiation oncologists who strive to take precise aim at tumors, and spare surrounding non-tumor tissues. For at least this reason, it is important that the treatment target be accurately tracked. There are at least two ways for tracking the treatment targets. Implanted devices are one way to track motion, but they require invasive procedures and have been associated with a 20%-50% greater risk of pneumothorax, or air in the pleural cavity, which can collapse or lead to infection of an already embattled lung. A preferred way, according to some experts, is to use anatomic surrogates—organs or structures, usually near the tumor—or externally placed surrogates whose movements can be used indirectly to track tumor motion. Previously, however, it has been found that surrogate correlation with the target can be poor.

Thus, embodiments of the invention use the principle of utilizing surrogates in a unique approach based on supervised learning to elicit relationships between the internal anatomy and surrogates and then employ the developed supervised learning model to prospectively predict the position of the treatment target. Certain embodiments permit tracking the position of the internal anatomy, such as a tumor, using the position of either externally placed surrogates (on the skin) or anatomical surrogates via supervised learning. In this method, a determination is made of complex positional relationships (that may vary temporally) between the internal anatomy and the surrogates using a small "training" data set. The learned positional relationship is then used to prospectively predict the position of the internal anatomy without direct measurement of the internal anatomy position.

Figure 8:
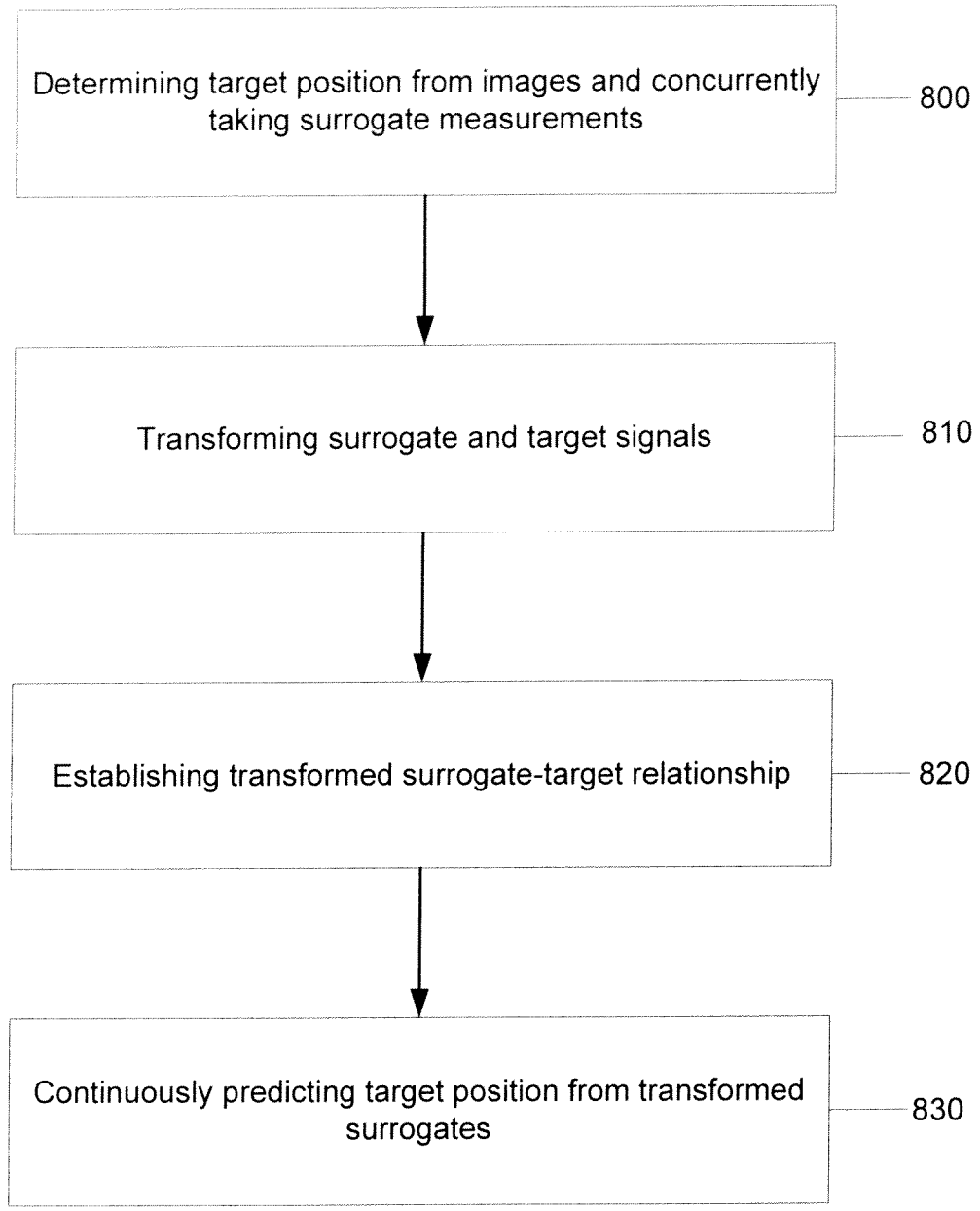
FIG. 8 is a flow diagram that illustrates a method for predicting the position of a target using surrogates.

Therefore, according to one embodiment, a method of predicting the position of a target site inside a human or other animal body in real time or near real time using surrogates is provided. FIG. 8 illustrates a flow diagram of an embodiment of the method. The method includes, at 800, determining the position of the target by continuous or periodic images. The images may be planar or volumetric images, such as x-rays, MRIs, and/or CT scans. In addition, at 800, surrogate measurements are concurrently taken in order to have synchronized measurements of the surrogate signal and the actual position of the target. The method further includes, at 810, transforming the surrogate measurements and the determined target position into different representations using mathematical operators. The operators can include, for example, latent variables or kernel transformations. At 820, the method includes establishing a special relationship between the transformed surrogate measurements and the transformed target position. The method may then include, at 830, continuously predicting the target position from the transformed surrogate measurements and the established relationship without explicitly measuring the position of the target.

Thus, embodiments of the invention avoid the poor correlation resulting from building a model directly between surrogates and target positions. Rather, embodiments of the invention transform the surrogate measurements and target positions using a mathematical operator, and build a relationship between those transformed surrogate positions and transformed target positions.

In some embodiments, the surrogate measurements can include: blood oxygen level measured using a pulse oxygen monitor, heart electrical activity measured using an electrocardiogram (EKG), brain electrical activity measured using an electroencephalogram (EEG), air flow measured using a spirometer, differential temperature of air flow measured using a thermocouple, and respiratory motion. The respiratory motion may be measured via the surface of the body using light in the visible or invisible portion of the spectrum. In another embodiment, the respiratory motion may be directly measured using an ultrasonic device, a strain gauge wrapped around the body, and/or on one or more objects resting on the surface of the body. The device for measuring the respiratory motion may include one or more camera(s), infrared camera(s), and/or scanning laser(s). Embodiments of the invention can simultaneously use one or more of these surrogate measurement techniques in any combination.

Therefore, embodiments of the invention overcome lack of good correlation between the surrogates and the treatment target, and prevent overfitting of the data used to establish the learned relationship between the transformed surrogates and treatment target. In other words, embodiments of the present invention do not assume or require good correlation between the surrogates and treatment target. Rather, a relationship is established between a transformed target and transformed surrogate signal. Additionally, embodiments of the invention can incorporate heterogeneous surrogates including varying scales and units. As such, embodiments of the invention are more accurate than conventional methods that implicitly rely on good correlation between surrogates and treatment targets.

In another embodiment, a method includes adjusting a radiotherapy treatment of a target site that moves during the treatment. The adjusting is performed by using a predicted position of the target site in real time or near real time. In one embodiment, the position is predicted by measurement of one or more surrogates irrespective of the quality (e.g., good or poor) and type (e.g., linear, non-linear or other) of relationship (e.g., correlation) between the surrogates and the target site. The position can be predicted without periodic or continual use of a direct measurement of the target site.

The measurement of the one or more surrogates, either synchronously or asynchronously or a combination thereof, may include one or more of the following: blood pressure using a blood pressure monitor, blood oxygen level using a pulse oxygen monitor, heart electrical activity using an EKG, brain electrical activity using an EEG, air flow using a spirometer, differential temperature of air flow using a thermocouple, respiratory motion using a strain gauge wrapped around the body, respiratory motion via direct measurement using a camera and visible light, respiratory motion via direct measurement using a visible or infrared camera, respiratory motion via direct measurement using a scanning laser, respiratory motion via direct measurement using an ultrasound device, respiratory motion via measurement of one or more object(s) resting on the surface of the body.

In one embodiment, the adjustment of the radiotherapy delivery includes altering the position of target site by moving the patient support device to the predicted position continuously throughout treatment. In another embodiment, the adjustment of the radiotherapy delivery includes adjusting the intensity pattern of the delivered radiation according to the predicted tumor position. The intensity adjustment can be done by using a multileaf collimation system, or by changing the intensity of the delivered pulses of radiation. In some embodiments, the adjustment of the radiotherapy delivery may include physically moving the radiation beam to the predicted location continuously throughout treatment.

7. Extensions and Alternatives

In the foregoing specification, the invention has been described with reference to specific embodiments thereof. It will, however, be evident that various modifications and changes may be made thereto without departing from the broader spirit and scope of the invention. The specification and drawings are, accordingly, to be regarded in an illustrative rather than a restrictive sense.

What is claimed is:

1. A method of predicting a position of a target site inside a body using surrogates, the method comprising:
    transforming surrogate measurements and target positions into different representations by applying an operator;
    establishing a special relationship between the transformed surrogate measurements and the transformed target positions; and
    continuously predicting the target position from the transformed surrogate measurements and the established special relationship.

2. The method of claim 1, wherein one of the surrogate measurements comprises blood oxygen level measured using a conventional pulse oxygen monitor.

3. The method of claim 1, wherein one of the surrogate measurements comprises heart electrical activity measured using an EKG.

4. The method of claim 1, wherein one of the surrogate measurements comprises brain electrical activity measured using an EEG.

5. The method of claim 1, wherein one of the surrogate measurements comprises air flow measured using a spirometer.

6. The method of claim 1, wherein one of the surrogate measurements comprises a differential temperature of air flow measured using a thermocouple.

7. The method of claim 1, wherein one of the surrogate measurements comprises respiratory motion.

8. The method of claim 7, wherein the respiratory motion is directly measured via the surface of the body.

9. The method of claim 8, wherein the direct measurement is done using light in a visible portion of the spectrum.

10. The method of claim 8, wherein the direct measurement is done using light in the invisible portion of the spectrum.

11. The method of claim 8, wherein the direct measurement is done using an ultrasonic device.

12. The method of claim 8, wherein the direct measurement is done on one or more object(s) resting on the surface of the body.

13. The method of claim 8, wherein the direct measurement is done using a strain gauge wrapped around the body.

14. The method of claim 7, wherein the respiratory motion is measured by a measuring device.

15. The method of claim 14, wherein the measuring device is one or more cameras.

16. The method of claim 14, wherein the measuring device is a scanning laser.

17. The method of claim 14, wherein the measuring device is an infrared camera.

18. A method, comprising:
adjusting a radiotherapy treatment of a target site that moves during the treatment,
wherein the adjusting comprises using a predicted position of a target site in real time or near real time,
wherein the position is predicted by measurement of one or more surrogates irrespective of the quality and type of relationship between the surrogates and the target site, and the position is predicted without periodic or continual use of a direct measurement of the target site.

19. The method of claim 18, wherein the measurement of the one or more surrogates, either synchronously or asynchronously or a combination thereof, comprises at least one of:
blood pressure using a conventional blood pressure monitor;
blood oxygen level using a conventional pulse oxygen monitor;
heart electrical activity using a standard EKG;
brain electrical activity using a standard EEG;
air flow using a spirometer;
differential temperature of air flow using a thermocouple;
respiratory motion using a strain gauge wrapped around the body;
respiratory motion via direct measurement using a camera and visible light;
respiratory motion via direct measurement using a visible or infrared camera;
respiratory motion via direct measurement using a scanning laser;
respiratory motion via direct measurement using an ultrasound device; and
respiratory motion via measurement of on one or more object(s) resting on the surface of the body.

20. The method of claim 18, wherein the adjusting of the radiotherapy delivery comprises altering a position of a target site by moving the patient support device to the predicted position continuously throughout treatment.

21. The method of claim 18, wherein the adjusting of the radiotherapy delivery comprises adjusting an intensity pattern of delivered radiation according to the predicted tumor position.

22. The method of claim 21, wherein the adjusting of the intensity pattern is done using a multileaf collimation system.

23. The method of claim 21, wherein the adjusting of the intensity pattern is done by changing the intensity of delivered pulses of radiation.

24. The method of claim 18, wherein the adjusting of the radiotherapy delivery comprises physically moving the radiation beam to the predicted location continuously throughout treatment.

* * * * *